US012806407B2

(12) United States Patent
Waxali

(10) Patent No.: US 12,806,407 B2
(45) Date of Patent: Nov. 24, 2026

(54) LVAD PLUG

(71) Applicant: THE METHODIST HOSPITAL, Houston, TX (US)

(72) Inventor: Neal Ainool Waxali, Missouri City, TX (US)

(73) Assignee: THE METHODIST HOSPITAL, Houston, TX (US)

( * ) Notice: Subject to any disclaimer, the term of this patent is extended or adjusted under 35 U.S.C. 154(b) by 211 days.

(21) Appl. No.: 18/579,261

(22) PCT Filed: Jul. 15, 2022

(86) PCT No.: PCT/US2022/037365

§ 371 (c)(1),
(2) Date: Jan. 12, 2024

(87) PCT Pub. No.: WO2023/288097

PCT Pub. Date: Jan. 19, 2023

(65) Prior Publication Data

US 2024/0325722 A1 Oct. 3, 2024

Related U.S. Application Data

(60) Provisional application No. 63/222,143, filed on Jul. 15, 2021.

(51) Int. Cl.

| | |
|---|---|
| ***A61M 60/863*** | (2021.01) |
| ***A61M 60/178*** | (2021.01) |
| ***A61M 60/865*** | (2021.01) |

(52) U.S. Cl.

CPC ........ *A61M 60/863* (2021.01); *A61M 60/178* (2021.01); *A61M 60/865* (2021.01)

(58) Field of Classification Search

CPC .............. A61M 60/178; A61M 60/232; A61M 60/863; A61M 60/865

See application file for complete search history.

(56) References Cited

U.S. PATENT DOCUMENTS

| | | | | |
|---|---|---|---|---|
| 6,319,231 B1 | 11/2001 | Andrulitis | | |
| 7,942,805 B2 * | 5/2011 | Shambaugh, Jr. .. | A61M 60/178 | 600/16 |

(Continued)

OTHER PUBLICATIONS

PCT/US2022/037365, International Search Report and Written Opinion of the International Searching Authority, mailed Nov. 1, 2022, 12 pages.

(Continued)

*Primary Examiner* — Scott Luan

(74) *Attorney, Agent, or Firm* — Meunier Carlin & Curfman LLC

(57) ABSTRACT

A plug for coupling to a suture ring may include a distal portion extending from a distal end toward a proximal end of the plug, and a proximal portion coupled to the distal portion and extending from the proximal end toward the distal end of the plug. The distal portion may include a distal cylindrical body centered on a central axis of the plug and configured for being received at least partially within a central opening of the suture ring, and the distal cylindrical body may have a first outer diameter. The proximal portion may include a proximal cylindrical body centered on the central axis of the plug and configured for extending over a proximal end of the suture ring when the distal cylindrical body is received at least partially within the central opening of the suture ring, and the proximal cylindrical body may have a second outer diameter that is greater than the first outer diameter.

20 Claims, 17 Drawing Sheets

(56) References Cited

U.S. PATENT DOCUMENTS

| | | | |
|---|---|---|---|
| 10,279,092 | B2 | 5/2019 | Andrus |
| 10,772,623 | B2 | 9/2020 | Hoarau et al. |
| 2018/0256799 | A1 | 9/2018 | Matthes et al. |
| 2021/0121677 | A1 | 4/2021 | Nguyen et al. |

OTHER PUBLICATIONS

Cohn, William E., et al. "A felt plug simplifies left ventricular assist device removal after successful bridge to recovery." The Journal of heart and lung transplantation 26.11 (2007): 1209-1211.

Ricklefs, Marcel, et al. "A new tool for an explantation strategy of HeartMate 3™ left ventricular assist device." Journal of Thoracic Disease 10.Suppl 15 (2018): S1825.

Hanke, Jasmin S., et al. "First-in-man explantation of a HeartMate 3 left ventricular assist device via customized plug." European Journal of Cardio-Thoracic Surgery 57.3 (2020): 604-606.

Lara, Diego A., et al. "Titanium plug closure after HeartWare ventricular assist device explantation in a 15-year-old girl: first US experience." Texas Heart Institute Journal 44.1 (2017): 66-69.

Shah, Shawn M., et al. "Construction of an Apical Plug for Explantation of HeartWare HVAD Left Ventricular Assist Device." The Annals of Thoracic Surgery 106.1 (2018): e15-e17.

Teelucksingh, Sachin, et al. "A novel problem, a tested solution: A case of an infected left ventricular titanium plug." Journal of Cardiac Surgery 35.11 (2020): 3179-3182.

* cited by examiner

LVAD PLUG

CROSS-REFERENCE TO RELATED APPLICATIONS

This application is a U.S. National Stage application filed under 35 U.S.C. § 371 of PCT/US2022/037365, filed Jul. 15, 2022, which claims priority to and the benefit of U.S. Provisional Patent Application No. 63/222,143, filed on Jul. 15, 2021, the disclosures of which are expressly incorporated herein by reference in their entirety.

FIELD OF THE DISCLOSURE

The present disclosure relates generally to medical devices and more particularly to plugs for coupling to a suture ring attached to the apex of the left ventricle of a heart of a patient, for example, to prevent blood loss from the left ventricle upon removal of a ventricular assist device from the suture ring, and related methods of using such plugs.

BACKGROUND OF THE DISCLOSURE

Left Ventricle Assist Devices (LVADs) are a promising therapeutic alternative to cardiac transplantation in patients with end-stage heart failure. LVADs are implanted as bridge to transplant, bridge to recovery and as destination therapy. The potential of cardiac recovery after mechanical support is the most desirable goal in the treatment of end-stage heart failure with LVADs, allowing device explantation and avoiding cardiac transplantation and lifelong mechanical support, with reduced complications.

Currently, depending on the cardiac pathology, only few patients can be weaned from ventricular assist devices. However, the growing number of patients undergoing LVAD implantation especially in earlier stages of congestive heart failure, new minimally invasive implantation techniques and a growing experience in the field of mechanical support could lead to an increase of cardiac recoveries.

Thus, there is a need for a device for effectively transitioning a patient from having an LVAD to cardiac recovery without complications and unnecessary strain on heart tissue.

SUMMARY OF THE DISCLOSURE

The present disclosure provides plugs for coupling to a suture ring attached to the apex of the left ventricle of a heart of a patient, for example, to prevent blood loss from the left ventricle upon removal of a ventricular assist device from the suture ring, and related methods of using such plugs.

In one aspect, a plug for coupling to a suture ring attached to the apex of the left ventricle of a heart of a patient is provided. In some implementations, the plug may include a distal portion extending from a distal end toward a proximal end of the plug, and a proximal portion coupled to the distal portion and extending from the proximal end toward the distal end of the plug. The distal portion may include a distal cylindrical body centered on a central axis of the plug and configured for being received at least partially within a central opening of the suture ring, and the distal cylindrical body may have a first outer diameter. The proximal portion may include a proximal cylindrical body centered on the central axis of the plug and configured for extending over a proximal end of the suture ring when the distal cylindrical body is received at least partially within the central opening of the suture ring, and the proximal cylindrical body may have a second outer diameter that is greater than the first outer diameter.

In some implementations, the plug also may include a cavity extending from the proximal end of the plug toward the distal end of the plug. In some implementations, the cavity may be defined entirely within the proximal portion. In some implementations, the cavity may extend through the proximal portion and into the distal portion. In some implementations, the cavity may be cylindrical. In some implementations, the cavity may be centered on the central axis of the plug. In some implementations, the cavity may be defined by a plurality of rounded edges.

In some implementations, the proximal portion also may include one or more recesses defined in an outer circumferential surface of the proximal cylindrical body. In some implementations, the one or more recesses may be configured for being engaged by a tool to facilitate placement of the plug relative to the suture ring or removal of the plug from the suture ring. In some implementations, the one or more recesses may include an annular proximal channel extending circumferentially around the central axis of the plug. In some implementations, the one or more recesses may include a plurality of holes each extending radially with respect to the central axis of the plug. In some implementations, the plurality of holes may include a pair of holes diametrically opposed to one another. In some implementations, the plurality of holes may include four or more holes disposed in a circumferential array around the central axis of the plug. In some implementations, the holes may be blind holes.

In some implementations, the distal portion also may include an annular distal channel extending circumferentially around the central axis of the plug. In some implementations, the annular distal channel may be configured for positioning within the central opening of the suture ring. In some implementations, the plug also may include an O-ring disposed at least partially within the annular distal channel and configured for forming a seal between the distal portion and a portion of the suture ring defining the central opening of the suture ring.

In some implementations, the proximal portion also may include an annular protrusion extending toward the distal end of the plug and encircling a portion of the distal cylindrical body. In some implementations, the annular protrusion and the portion of the distal cylindrical body may define an annular space therebetween, and the annular space may be configured for receiving a portion of the suture ring therein such that the annular protrusion encircles the portion of the suture ring. In some implementations, the proximal portion also may include a plurality of thru holes each extending radially with respect to the central axis of the plug from an outer circumferential surface of the annular protrusion to the annular space. In some implementations, each of the thru holes may be configured for receiving a fastener therethrough. In some implementations, the plug also may include a plurality of fasteners each configured for extending through one of the thru holes and engaging the portion of the suture ring. In some implementations, the thru holes may be threaded, and the fasteners may be threaded. In some implementations, the thru holes may be disposed in a circumferential array around the central axis of the plug.

In another aspect, a system is provided. In some implementations, the system may include a suture ring and a plug. The suture ring may include an adjustable clamp disposed around a central opening of the suture ring and configured for adjusting between an unlocked configuration and a locked configuration, and a fastener coupled to the adjustable clamp and configured for adjusting the adjustable clamp between the unlocked configuration and the locked configuration. The plug may include a distal portion extending from a distal end of the plug toward a proximal end of the plug, and a proximal portion coupled to the distal portion and extending from the proximal end of the plug toward the distal end of the plug. The distal portion may include a distal cylindrical body centered on a central axis of the plug and configured for being received at least partially within the central opening of the suture ring, and the distal cylindrical body may have a first outer diameter. The proximal portion may include a proximal cylindrical body centered on the central axis of the plug and configured for extending over a proximal end of the suture ring when the distal cylindrical body is received at least partially within the central opening of the suture ring, and the proximal cylindrical body may have a second outer diameter that is greater than the first outer diameter. The adjustable clamp may be configured for securing the plug to the suture ring when the distal cylindrical body is received at least partially within the central opening of the suture ring and the adjustable clamp is in the locked configuration.

In still another aspect, a system is provided. In some implementations, the system may include a suture ring, a plug, and a plurality of fasteners. The suture ring may include a proximal flange disposed around a central opening of the suture ring, and a tubular body coupled to the proximal flange and disposed around the central opening of the suture ring. The plug may include a distal portion extending from a distal end of the plug toward a proximal end of the plug, and a proximal portion coupled to the distal portion and extending from the proximal end of the plug toward the distal end of the plug. The distal portion may include a distal cylindrical body centered on a central axis of the plug and configured for being received at least partially within the central opening of the suture ring, and the distal cylindrical body may have a first outer diameter. The proximal portion may include a proximal cylindrical body and an annular protrusion. The proximal cylindrical body may be centered on the central axis of the plug and configured for extending over the proximal flange of the suture ring when the distal cylindrical body is received at least partially within the central opening of the suture ring, and the proximal cylindrical body may have a second outer diameter that is greater than the first outer diameter. The annular protrusion may extend toward the distal end of the plug and encircle a portion of the distal cylindrical body such that the annular protrusion and the portion of the distal cylindrical body define an annular space therebetween. The annular space may be configured for receiving the proximal flange and at least a portion of the tubular body of the suture ring therein when the distal cylindrical body is received at least partially within the central opening of the suture ring. The fasteners may be configured for extending through a plurality thru holes defined in the annular protrusion and engaging the tubular body of the suture ring to secure the plug to the suture ring when the distal cylindrical body is received at least partially within the central opening of the suture ring.

These and other aspects and improvements of the present disclosure will become apparent to one of ordinary skill in the art upon review of the following detailed description when taken in conjunction with the several drawings and the appended claims.

Figure 1:
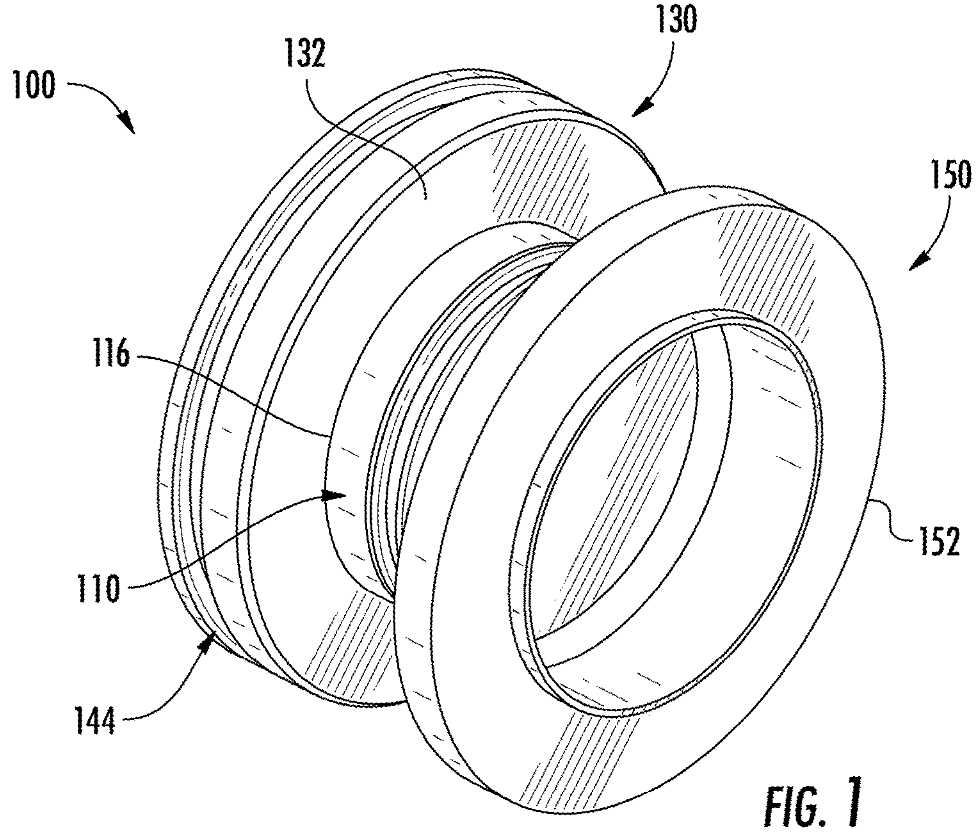
FIG. 1 is a perspective view of an example plug and an example suture ring in accordance with implementations of the present disclosure, showing the plug and the suture ring separated from one another.

The detailed description is set forth with reference to the accompanying drawings. The drawings are provided for purposes of illustration only and merely depict example implementations of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various implementations may utilize elements or components other than those illustrated in the drawings, and some elements and/or components may not be present in various implementations. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

Overview

The devices, systems, and methods disclosed herein provide for a plug configured to be coupled to a suture ring that is attached to the apex of the left ventricle of a patient's heart. The suture ring, for example, may have been previously sutured to the patient's heart and coupled to an LVAD during LVAD implantation surgery. If a doctor decides that the LVAD is no longer needed or that the heart could possibly survive without the LVAD, the LVAD may be decoupled from the suture ring and surgically removed. The suture ring may be left on the patient's heart and recoupled (or newly coupled) to the plug to seal the patient's heart. If necessary, the plug can later be easily decoupled from the suture ring and the LVAD can again be coupled to the suture ring on the patient's heart.

Various benefits and advantages of the plugs, systems, and methods provided herein over existing devices and techniques will be appreciated by those of ordinary skill in the art from the following description and the appended drawings.

Example LVAD Plugs

Figure 10:
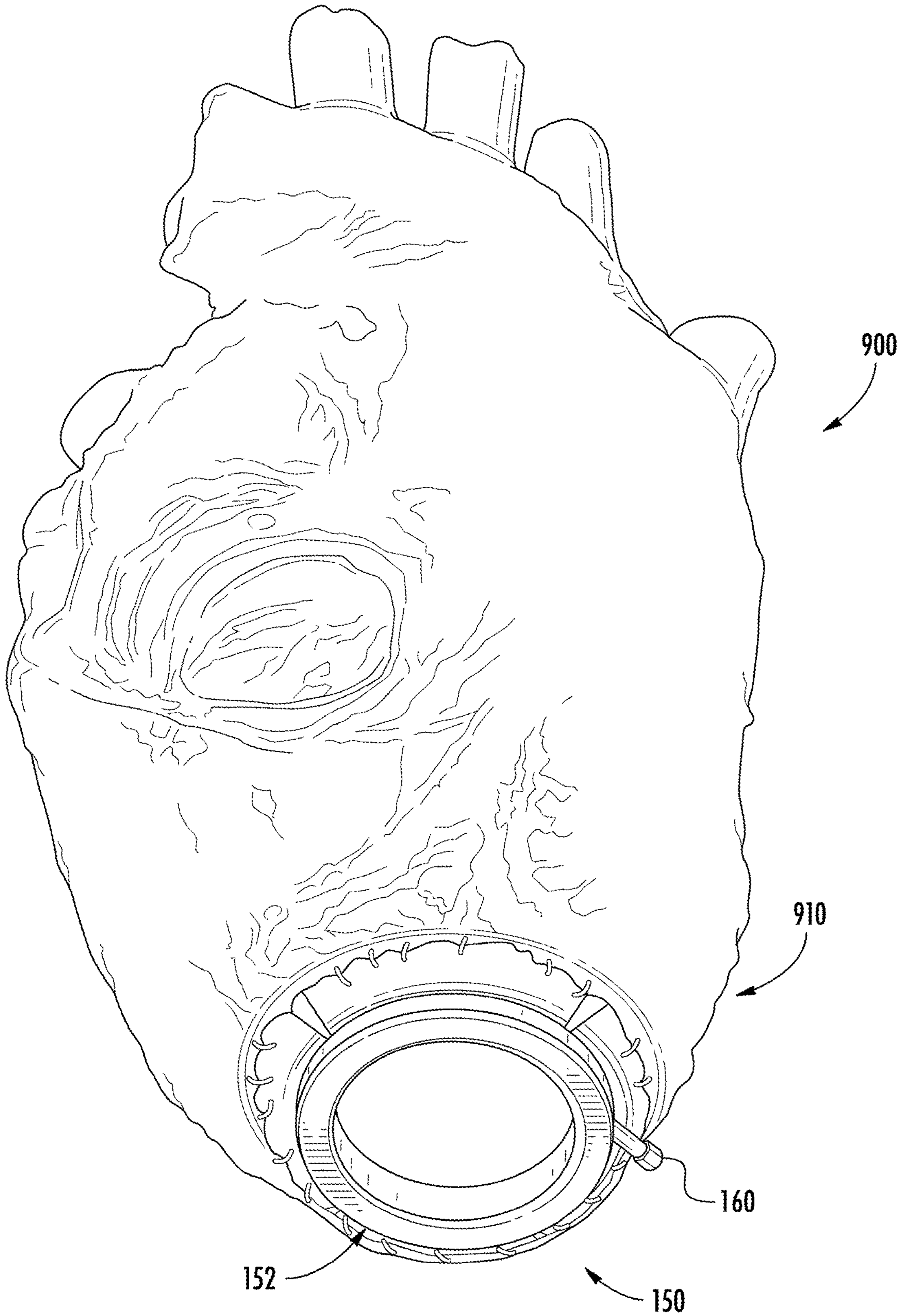
FIG. 10 is a perspective view of the suture ring of FIG. 1 coupled to a heart.

Referring now to the drawings, FIGS. 1-8 illustrate an example plug 100 (which also may be referred to as a "closure device," an "occlusion device," or simply a "device") in accordance with implementations of the disclosure. The plug 100 may be configured for use with a suture ring 150, which may be attached to a patient's heart 900 by suturing, as shown in FIG. 10, for coupling an LVAD at the apex of the left ventricle 910. As described herein, the plug 100 may be configured for coupling to the suture ring 150, for example, upon removal of the LVAD therefrom, to prevent blood loss from the left ventricle 910 through the suture ring 150. Although the plug 100 is shown being used with suture ring 150, it will be appreciated that the plug 100 may be configured for use with other types of suture rings, in accordance with other implementations.

As shown, the plug 100 may have a proximal end 102 and a distal end 104 disposed opposite one another along a central axis of the plug 100. In some implementations, as shown, the plug 100 may be symmetric about the central axis of the plug 100. The plug 100 may include a distal portion 110 (which also may be referred to as an "anchoring portion" or a "first portion") and a proximal portion 130 (which also may be referred to as a "blocking portion" or a "second portion") coupled to one another. The distal portion 110 may extend from the distal end 104 toward the proximal end 102, and the proximal portion 130 may extend from the proximal end 102 toward the distal end 104. The distal portion 110 may be configured to engage with the suture ring 150 such that the distal portion 110 and the proximal portion 130 prevent blood loss from the left ventricle 910 while withstanding the beating heart pressure of the patient's heart 900. In some implementations, as shown, the distal portion 110 and the proximal portion 130 may be integrally formed with one another. In some implementations, the plug 100 may be formed of a metal, although other suitable materials may be used. In some implementations, the plug 100 may be formed of titanium, such as grade 5 titanium alloy (ASTM B348).

Figure 2:
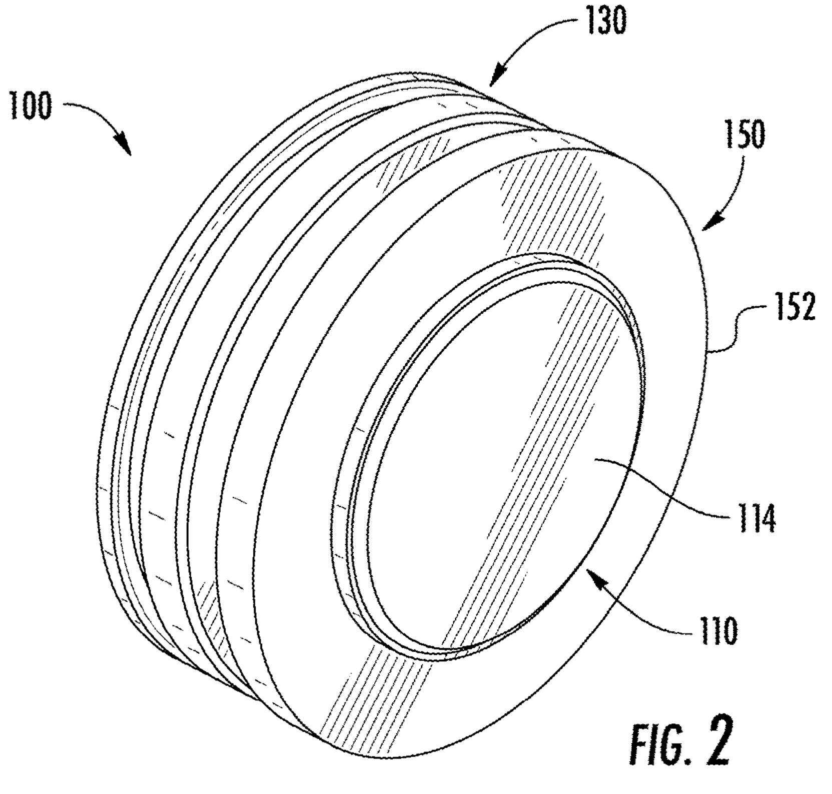
FIG. 2 is a perspective view of the plug and the suture ring of FIG. 1 coupled together.
Figure 3:
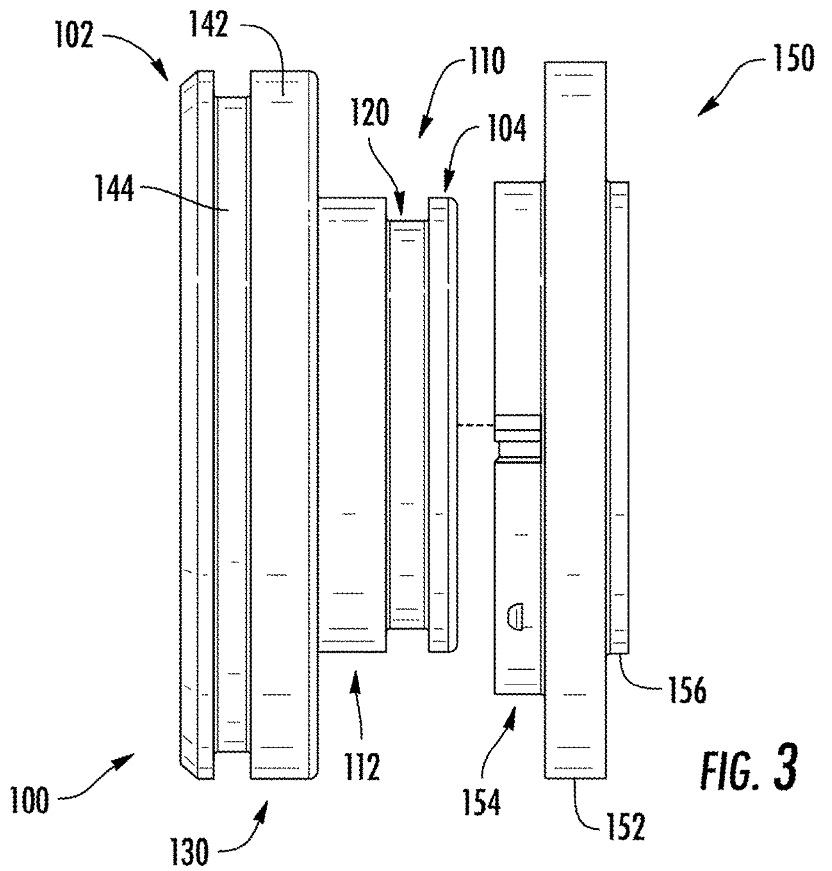
FIG. 3 is a side view of the plug and the suture ring of FIG. 1 separated from one another.
Figure 4:
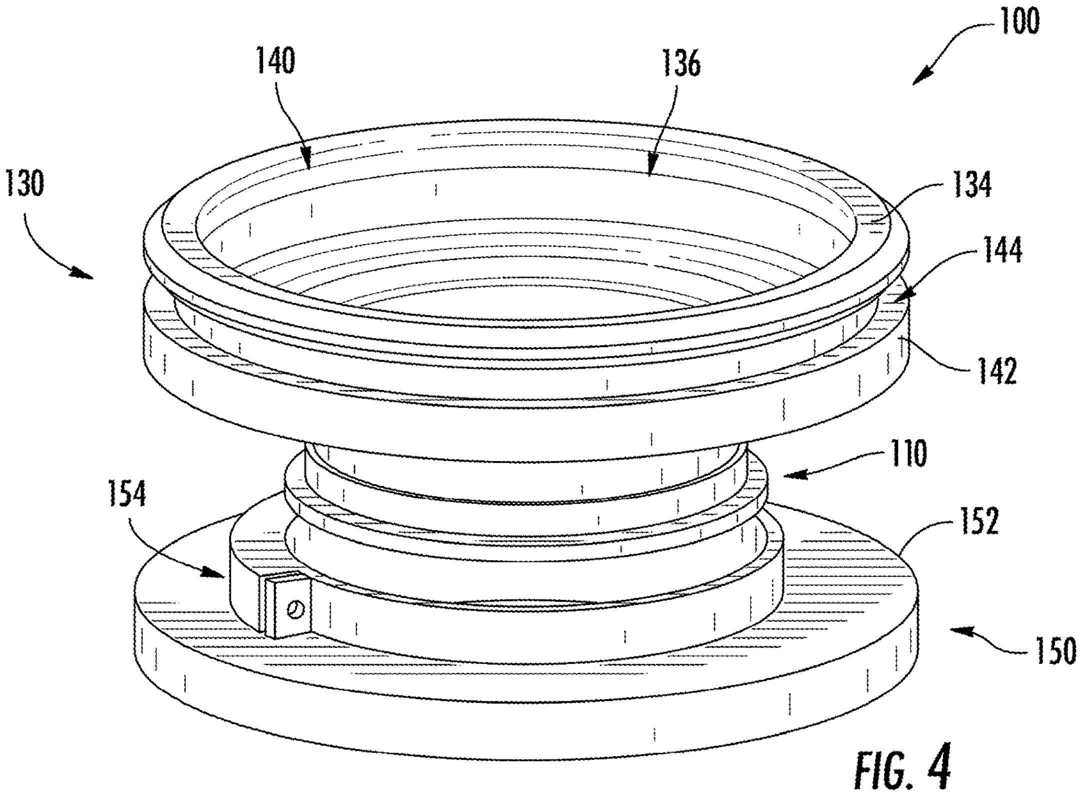
FIG. 4 is a top perspective view of the plug and the suture ring of FIG. 1 separated from one another.
Figure 5:
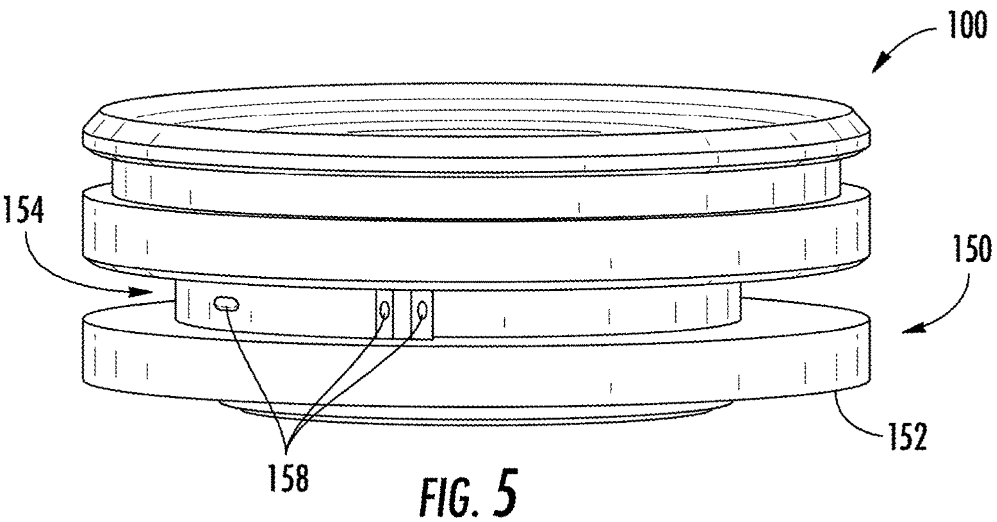
FIG. 5 is a top perspective view of the plug and the suture ring of FIG. 1 coupled together.
Figure 6:
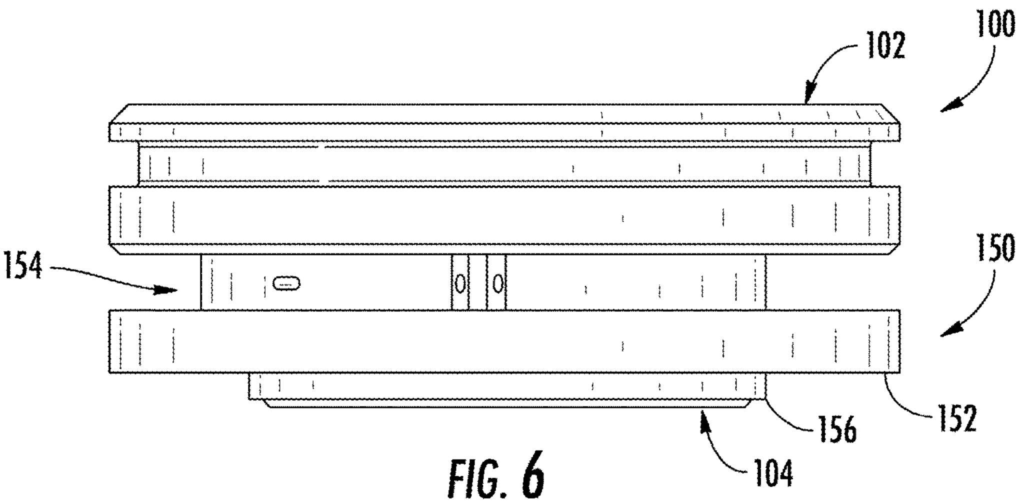
FIG. 6 is a side view of the plug and the suture ring of FIG. 1 coupled together.
Figure 7:
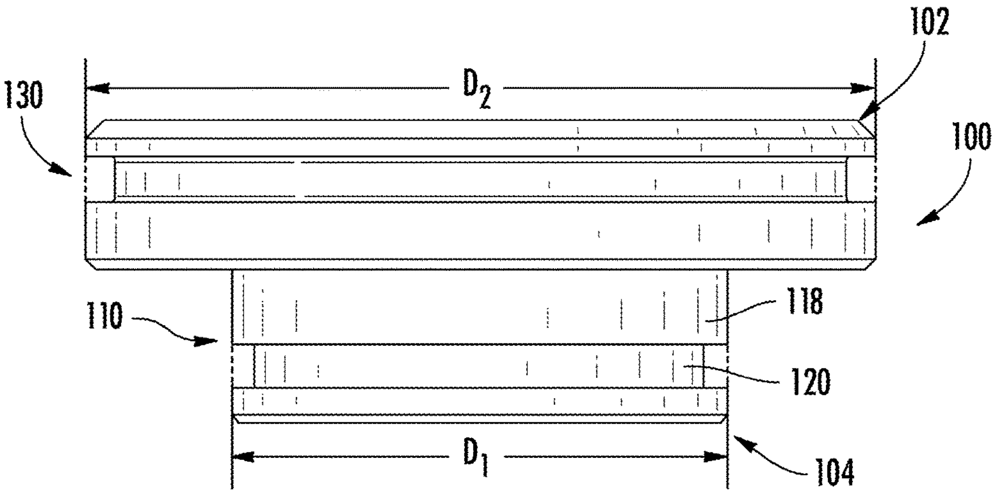
FIG. 7 is a side view of the plug of FIG. 1.
Figure 8:
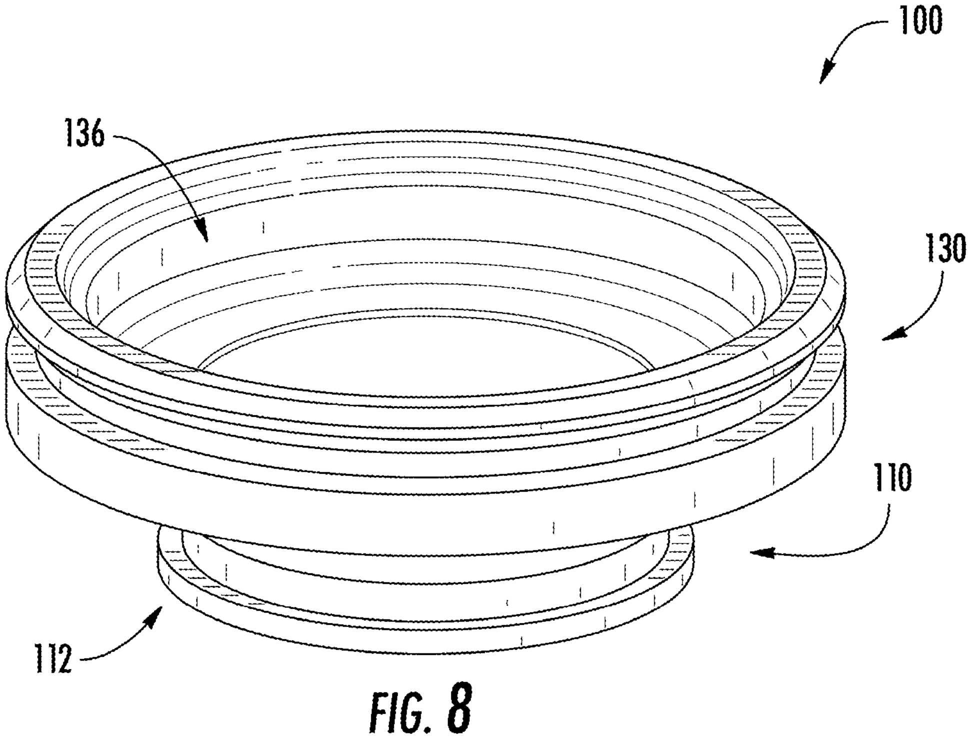
FIG. 8 is a top perspective view of the plug of FIG. 1.

The distal portion 110 may include a distal cylindrical body 112 having a first diameter $D_1$, a first surface 114 (which also may be referred to as a "distal surface"), a second surface 116 (which also may be referred to as a "proximal surface") spaced and disposed opposite the first surface 114 in the direction of the central axis of the plug 100, and a third surface 118 (which also may be referred to as an "outer circumferential surface") that extends from the first surface 114 to the second surface 116. As shown, the distal cylindrical body 112 may be centered on the central axis of the plug 100 and configured for being received at least partially within the central opening of the suture ring 150. In some implementations, the first surface 114 of the distal portion 110 may be smooth, highly polished, and, when the plug 100 is coupled with the suture ring 150, flush with the distal end of the suture ring 150 inside the patient's left ventricle 910, as shown in FIG. 2. In other implementations, the first surface 114 of the distal portion 110 may extend beyond the distal end of the suture ring 150 when the plug 100 is coupled with the suture ring 150.

As shown, the third surface 118 of the distal portion 110 may define an annular distal channel 120 that extends circumferentially along at least a portion of the third surface 118 of the distal portion 110. In some implementations, the annular distal channel 120 may be configured for positioning within the central opening of the suture ring 150 when the plug 100 is coupled to the suture ring 150. In some implementations, the plug 100 also may include an O-ring formed of an elastomeric material, such as silicone, that is disposed at least partially within the annular distal channel 120 and configured for forming a seal between the distal portion 110 and a portion of the suture ring 150 defining the central opening of the suture ring 150. In other implementations, the distal portion 110 may include a silicate coating in addition to or instead of the O-ring disposed within the annular distal channel 120 to promote a tight seal between the suture ring 150 and the distal portion 110. In some implementations, as shown, the distal end of the distal portion 110 may be chamfered to avoid harsh sharp edges that could be harmful to the heart or internal organs of the patient.

The proximal portion 130 may include a proximal cylindrical body having a first surface 132 (which also may be referred to as a "distal surface"), a second surface 134 (which also may be referred to as a "proximal surface") spaced and disposed opposite the first surface 132 in the direction of the central axis of the plug 100, and a third surface 142 (which also may be referred to as an "outer circumferential surface") that extends from the first surface 132 to the second surface 134. As shown, the proximal cylindrical body of the proximal portion 130 may have a second diameter $D_2$ that greater than the first diameter $D_1$ of the distal cylindrical body 112 of the distal portion 110. In this manner, proximal cylindrical body of the proximal portion 130 may extend radially outward relative to the distal portion 110. As shown, the proximal cylindrical body may be centered on the central axis of the plug 100 and configured for extending over the proximal end of the suture ring 150 when the distal cylindrical body 112 is received at least partially within the central opening of the suture ring 150. In some implementations, as shown, the first surface 132 of the proximal cylindrical body of the proximal portion 130 may be adjacent and directly coupled to the second surface 116 of the distal cylindrical body 112 of the distal portion 110. In some implementations, the first surface 132 and the second surface 134 of the blocking portion 130 may be continuous. Also, similar to the distal end of the distal portion 110, the proximal and distal ends of the proximal portion 130 may be chamfered to avoid harsh sharp edges that could be harmful to the heart or internal organs of the patient.

As shown, the plug 100 may include a cavity 136 extending from the proximal end 102 toward the distal end 104 of the plug 100. The cavity 136 may extend at least partially into the proximal portion 130. In some implementations, the cavity 136 may be defined entirely within the proximal portion 130. In other implementations, the cavity 136 may extend through the proximal portion 130 and into the distal portion 110 but may terminate at a location spaced apart from the distal end of the distal portion 110. In some implementations, as shown, the cavity 136 may be cylindrical. In some implementations, the cavity 136 may have different regions having different diameters, for example, with a larger diameter region defined in the proximal portion 130 and a smaller diameter region defined in the distal portion 110. The size, shape, and extend of the cavity 136 may be selected to minimize the weight of the plug 100 in order to not put excessive strain on the heart 900 when the plug 100 is coupled to the suture ring 150, while maintaining the structural integrity of the plug 100. In some implementations, as shown, the cavity 136 may be defined by a plurality of smooth, rounded edges 140 that extend circumferentially around the cavity 136.

The plug 100 may include one or more features that are configured to be engaged by a tool to facilitate positioning of the plug 100 during implantation or removal of the plug 100. For example, the proximal portion 130 may include one or more recesses defined in the third surface 142 of the proximal cylindrical body and configured for being engaged by a tool to facilitate placement of the plug 100 relative to the suture ring 150 or removal of the plug 100 from the suture ring 150. In some implementations, as shown, the one or more recesses may include an annular proximal channel 144 that extends circumferentially along at least a portion of the third surface 142 of the proximal portion 130.

As shown, the suture ring 150 may include a flange 152 (which also may be referred to as a "base flange" or a "base"), an adjustable clamp 154 (which also may be referred to as a "locking clamp" or an "adjustable flange") extending proximally from the flange 152 and defining the proximal end of the suture ring 150, and an annular protrusion 156 extending distally from the flange 152 and defining the distal end of the suture ring 150. In some implementations, the flange 152, the adjustable clamp 154, and the annular protrusion 156 may be integrally formed with one another. In some implementations; the flange 152, the adjustable clamp 154, and the annular protrusion 156 may be formed of a metal, such as titanium, although other suitable materials may be used. The flange 152 may encircle the central opening of the suture ring 150 and be configured for engaging the outer surface of the patient's heart 900 when the suture ring 150 is attached thereto. In some implementations, the flange 152 may include a plurality of openings extending therethrough to facilitate suturing of the suture ring 150 to the heart 900. In some implementations, the suture ring 150 may include a fabric material that covers at least a portion of the flange 152 to facilitate suturing of the suture ring 150 to the heart 900, as shown in FIG. 10. The adjustable clamp 154 may extend around the central opening of the suture ring 150 and be configured for adjusting between an unlocked configuration, to allow for insertion or removal of the plug 100 or an LVAD, and a locked configuration, to secure the plug 100 or an LVAD to the suture ring 150. In some implementations, as shown, the adjustable clamp 154 may be formed as a C-shaped clamp having a plurality of fastener openings 158 that are aligned with one another and configured for receiving a fastener 160, such as a threaded rod or screw. The adjustable clamp 154 may include a fixed portion that is fixedly attached to the flange 152 and a movable portion that is detached from the flange 152 and able to bend or otherwise move relative to the fixed portion. One of the fastener openings 158 may be defined in the fixed portion, and another fastener opening 158 may be defined in the movable portion. In this manner, the fastener 160 may be coupled to the adjustable clamp 154 and configured for adjusting the adjustable clamp 154 between the unlocked configuration and the locked configuration. As shown, the suture ring 150 generally corresponds to the suture ring of the Medtronic™ Heartware LVAD.

The plug 100 may be coupled to the suture ring 150 by inserting the distal portion 110 at least partially within the central opening of the suture ring 150 while the adjustable clamp 154 is in the unlocked configuration, and then adjusting the adjustable clamp 154 to the locked configuration by tightening the fastener 160. In this manner, the adjustable clamp 154 may be tightened to securely engage the third surface 118 of the distal portion 110 in the same manner as the adjustable clamp 154 engages an inlet tube of an LVAD. The third surface 118 of the distal portion receives pressure from the tightening of the adjustable clamp 154 of the suture ring 150 such that the pressure from the suture ring 150 couples the suture ring 150 to the distal portion 110 of the plug 100. When the plug 100 is used following removal of an LVAD from the suture ring 150 previously sutured to the cardiac tissue during the LVAD implantation, the tissue typically has healed around the suture ring 150, with tissue growth forming a strong bond between the suture ring 150 and the cardiac tissue of the heart 900. An advantageous aspect of the described approach for coupling the plug 100 to the suture ring 150 is that the technique does not require suturing or any involvement or disruption of the surrounding cardiac tissue of the heart 900. Furthermore, if the patient ever requires LVAD implantation again, the plug 100 can simply be removed from the suture ring 150 without any involvement or disruption of the surrounding cardiac tissue. Although the illustrated implementation provides one example of features for coupling the plug 100 to the suture ring 150, in other implementations, the suture ring 150 may include various other types any fastening features capable of coupling the plug 100 to the suture ring 150 without involving or disrupting the surrounding cardiac tissue.

Figure 9:
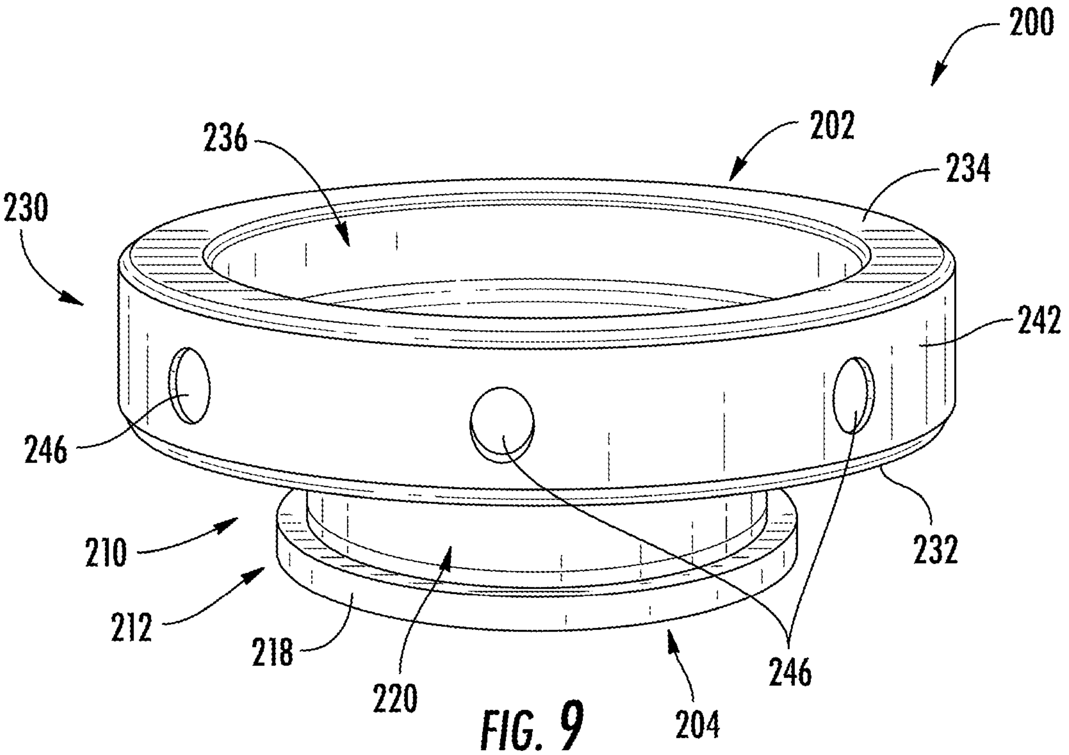
FIG. 9 is a top perspective view of an example plug in accordance with implementations of the present disclosure, as may be used with the suture ring of FIG. 1.

FIG. 9 illustrates an example plug 200 (which also may be referred to as a "closure device," an "occlusion device," or simply a "device") in accordance with implementations of the disclosure. Certain similarities and differences between the plug 200 and the plug 100 will be appreciated from the drawings and the following description. Particular differences relate to features used for grasping the plug 200 with a tool for insertion or removal of the plug 200. The plug 200 may be configured for use with a suture ring 150, which may be attached to a patient's heart 900 by suturing, as shown in FIG. 10, for coupling an LVAD at the apex of the left ventricle 910. As described herein, the plug 200 may be configured for coupling to the suture ring 150, for example, upon removal of the LVAD therefrom, to prevent blood loss from the left ventricle 910 through the suture ring 150. Although the plug 200 is shown being used with suture ring 150, it will be appreciated that the plug 200 may be configured for use with other types of suture rings, in accordance with other implementations.

As shown, the plug 200 may have a proximal end 202 and a distal end 204 disposed opposite one another along a central axis of the plug 200. In some implementations, as shown, the plug 200 may be symmetric about the central axis of the plug 200. The plug 200 may include a distal portion 210 (which also may be referred to as an "anchoring portion" or a "first portion") and a proximal portion 230 (which also may be referred to as a "blocking portion" or a "second portion") coupled to one another. The distal portion 210 may extend from the distal end 204 toward the proximal end 202, and the proximal portion 230 may extend from the proximal end 202 toward the distal end 204. The distal portion 210 may be configured to engage with the suture ring 150 such that the distal portion 210 and the proximal portion 230 prevent blood loss from the left ventricle 910 while withstanding the beating heart pressure of the patient's heart 900. In some implementations, as shown, the distal portion 210 and the proximal portion 230 may be integrally formed with one another. In some implementations, the plug 200 may be formed of a metal, although other suitable materials may be used. In some implementations, the plug 200 may be formed of titanium, such as grade 5 titanium alloy (ASTM B348).

The distal portion 210 may include a distal cylindrical body 212 having a first diameter, a first surface 214 (which also may be referred to as a "distal surface"), a second surface 216 (which also may be referred to as a "proximal surface") spaced and disposed opposite the first surface 214 in the direction of the central axis of the plug 200, and a third surface 218 (which also may be referred to as an "outer circumferential surface") that extends from the first surface 214 to the second surface 216. As shown, the distal cylindrical body 212 may be centered on the central axis of the plug 200 and configured for being received at least partially within the central opening of the suture ring 150. In some implementations, the first surface 214 of the distal portion 210 may be smooth, highly polished, and, when the plug 200 is coupled with the suture ring 150, flush with the distal end of the suture ring 150 inside the patient's left ventricle 910. In other implementations, the first surface 214 of the distal portion 210 may extend beyond the distal end of the suture ring 150 when the plug 100 is coupled with the suture ring 150.

As shown, the third surface 218 of the distal portion 210 may define an annular distal channel 220 that extends circumferentially along at least a portion of the third surface 218 of the distal portion 210. In some implementations, the annular distal channel 220 may be configured for positioning within the central opening of the suture ring 150 when the plug 200 is coupled to the suture ring 150. In some implementations, the plug 200 also may include an O-ring formed of an elastomeric material, such as silicone, that is disposed at least partially within the annular distal channel 220 and configured for forming a seal between the distal portion 210 and a portion of the suture ring 150 defining the central opening of the suture ring 150. In other implementations, the distal portion 210 may include a silicate coating in addition to or instead of the O-ring disposed within the annular distal channel 220 to promote a tight seal between the suture ring 150 and the distal portion 210. In some implementations, as shown, the distal end of the distal portion 210 may be chamfered to avoid harsh sharp edges that could be harmful to the heart or internal organs of the patient.

The proximal portion 230 may include a proximal cylindrical body having a first surface 232 (which also may be referred to as a "distal surface"), a second surface 234 (which also may be referred to as a "proximal surface") spaced and disposed opposite the first surface 232 in the direction of the central axis of the plug 100, and a third surface 242 (which also may be referred to as an "outer circumferential surface") that extends from the first surface 232 to the second surface 234. As shown, the proximal cylindrical body of the proximal portion 230 may have a second diameter that is greater than the first diameter of the distal cylindrical body 212 of the distal portion 210. In this manner, the proximal cylindrical body of the proximal portion 230 may extend radially outward relative to the distal portion 210. As shown, the proximal cylindrical body may be centered on the central axis of the plug 200 and configured for extending over the proximal end of the suture ring 150 when the distal cylindrical body 212 is received at least partially within the central opening of the suture ring 150. In some implementations, as shown, the first surface 232 of the proximal cylindrical body of the proximal portion 230 may be adjacent and directly coupled to the second surface 216 of the distal cylindrical body 212 of the distal portion 210. In some implementations, the first surface 232 and the second surface 234 of the blocking portion 230 may be continuous. Also, similar to the distal end of the distal portion 210, the proximal and distal ends of the proximal portion 230 may be chamfered to avoid harsh sharp edges that could be harmful to the heart or internal organs of the patient.

As shown, the plug 200 may include a cavity 236 extending from the proximal end 202 toward the distal end 204 of the plug 200. The cavity 236 may extend at least partially into the proximal portion 230. In some implementations, the cavity 236 may be defined entirely within the proximal portion 230. In other implementations, the cavity 236 may extend through the proximal portion 230 and into the distal portion 210 but may terminate at a location spaced apart from the distal end of the distal portion 210. In some implementations, as shown, the cavity 236 may be cylindrical. In some implementations, the cavity 236 may have different regions having different diameters, for example, with a larger diameter region defined in the proximal portion 230 and a smaller diameter region defined in the distal portion 210. The size, shape, and extend of the cavity 236 may be selected to minimize the weight of the plug 200 in order to not put excessive strain on the heart 900 when the plug 200 is coupled to the suture ring 150, while maintaining the structural integrity of the plug 200. In some implementations, as shown, the cavity 236 may be defined by a plurality of smooth, rounded edges that extend circumferentially around the cavity 236.

The plug 200 may include one or more features that are configured to be engaged by a tool to facilitate positioning of the plug 200 during implantation or removal of the plug 200. For example, the proximal portion 230 may include one or more recesses defined in the third surface 242 of the proximal cylindrical body and configured for being engaged by a tool to facilitate placement of the plug 200 relative to the suture ring 150 or removal of the plug 200 from the suture ring 150. In some implementations, as shown, the one or more recesses may include a plurality of holes 246 each extending radially with respect to the central axis of the plug 200. In some implementations, the plurality of holes 246 may include at least one, or several, pairs of the holes 246 diametrically opposed to one another. In some implementations, the plurality of holes 246 may include four or more of the holes 246 disposed in a circumferential array around the central axis of the plug 200. Although the illustrated implementation includes eight of the holes 246, a greater or lesser number of the holes 246 may be used. In some implementations, as shown, the holes 246 may be blind holes that terminate at locations spaced apart from the cavity 236. The holes 246 may be configured for receiving mating features of a tool, such as the tools 700, 800 described below. In some implementations, the holes 246 may not be diametrically opposed to one another, depending on the tool intended to be used with the plug 200.

Figure 11:
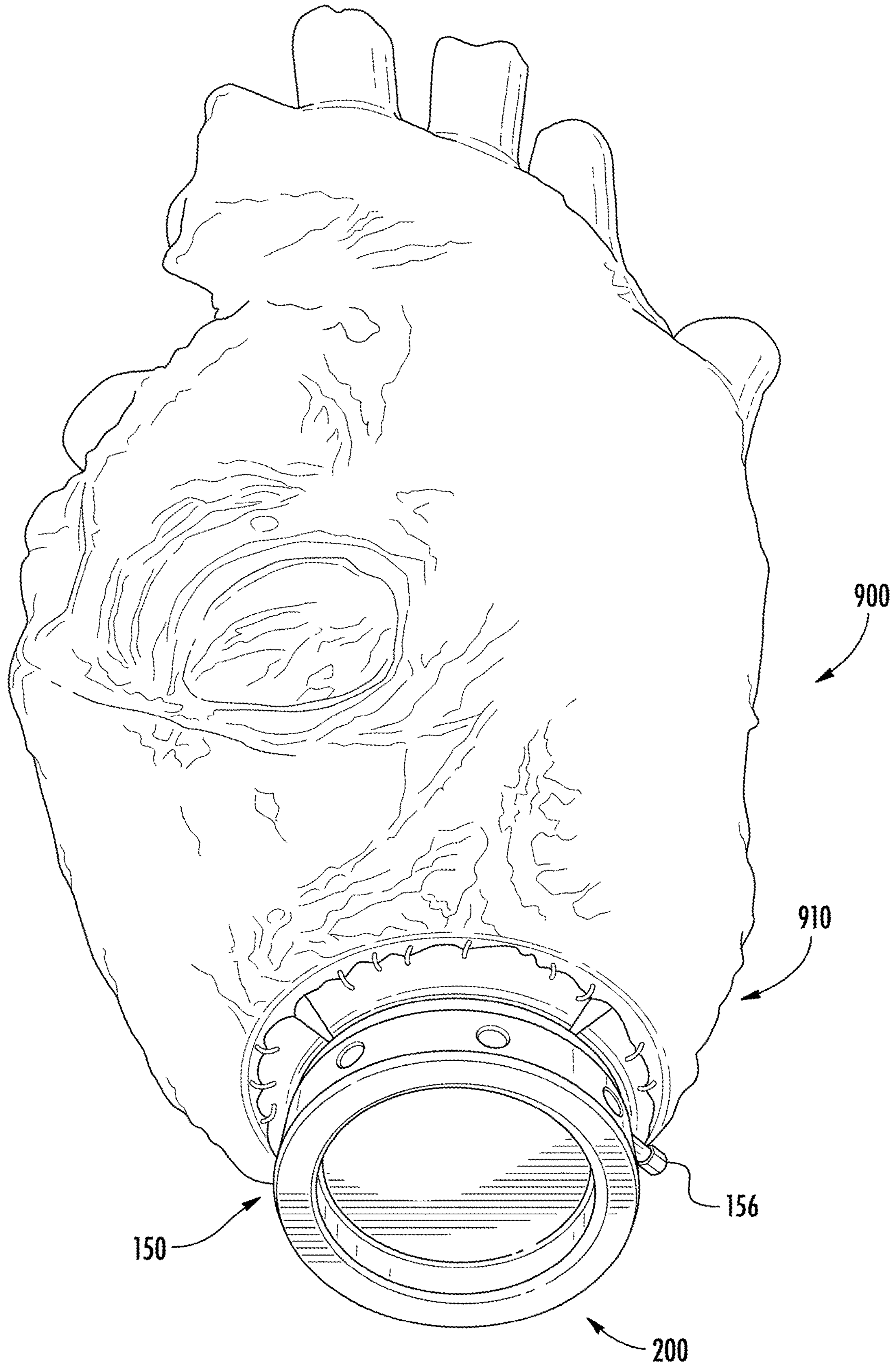
FIG. 11 is a perspective view of the plug of FIG. 9 and the suture ring of FIG. 1 coupled to a heart.
Figure 12:
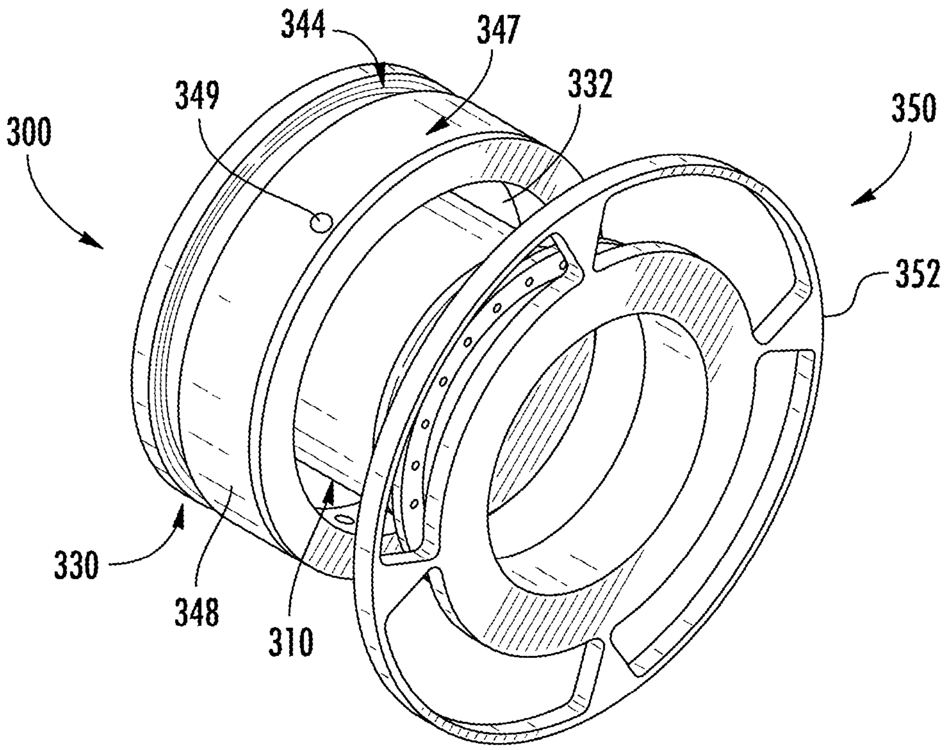
FIG. 12 is a perspective view of an example plug and an example suture ring in accordance with implementations of the present disclosure, showing the plug and the suture ring separated from one another.
Figure 13:
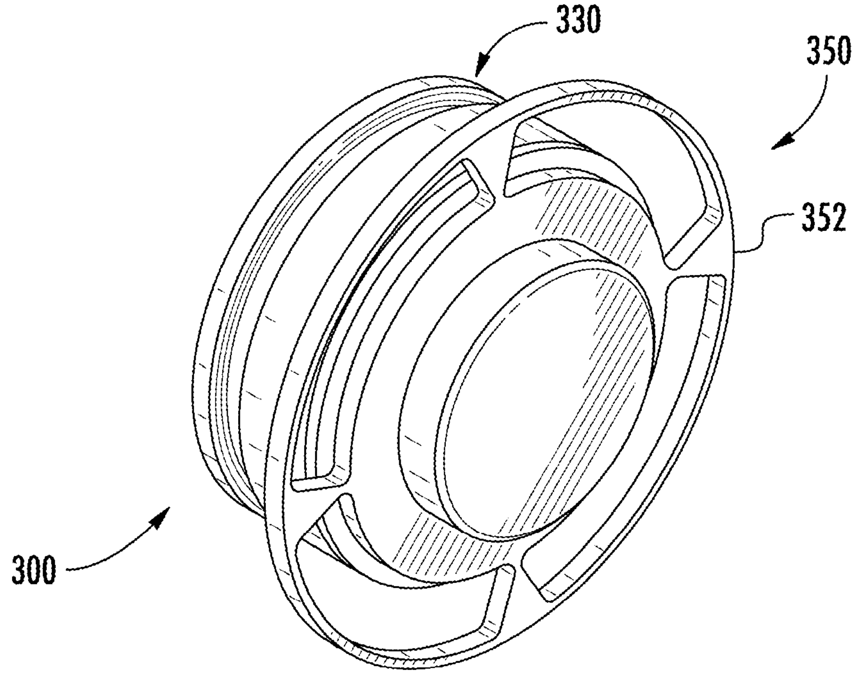
FIG. 13 is a perspective view of the plug and the suture ring of FIG. 12 coupled together.
Figure 14:
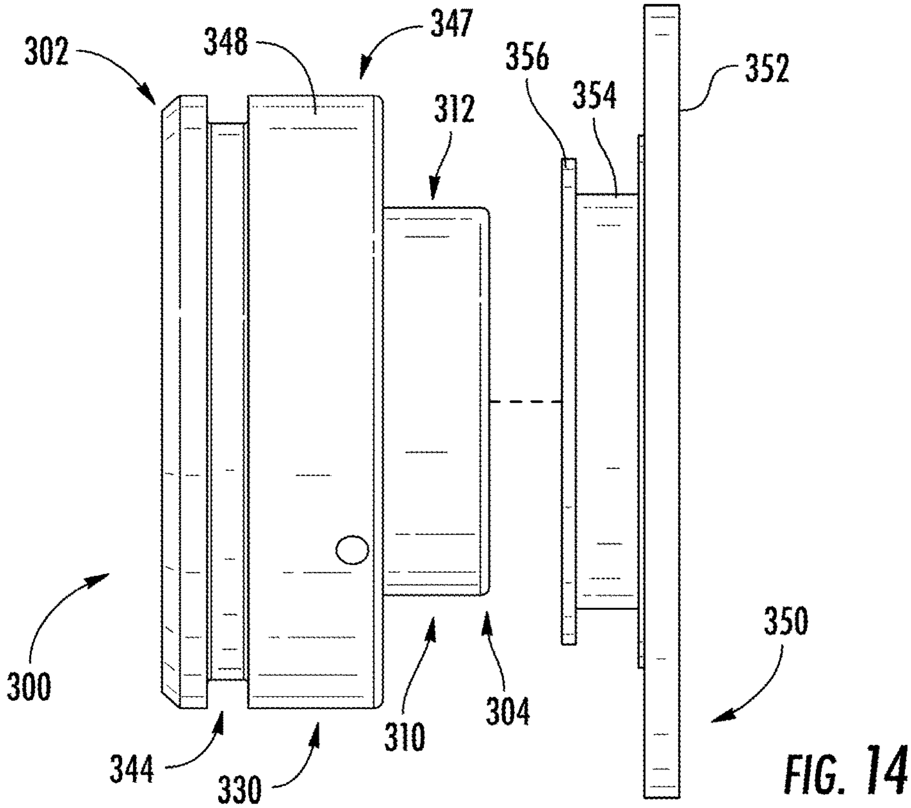
FIG. 14 is a side view of the plug and the suture ring of FIG. 12 separated from one another.
Figure 15:
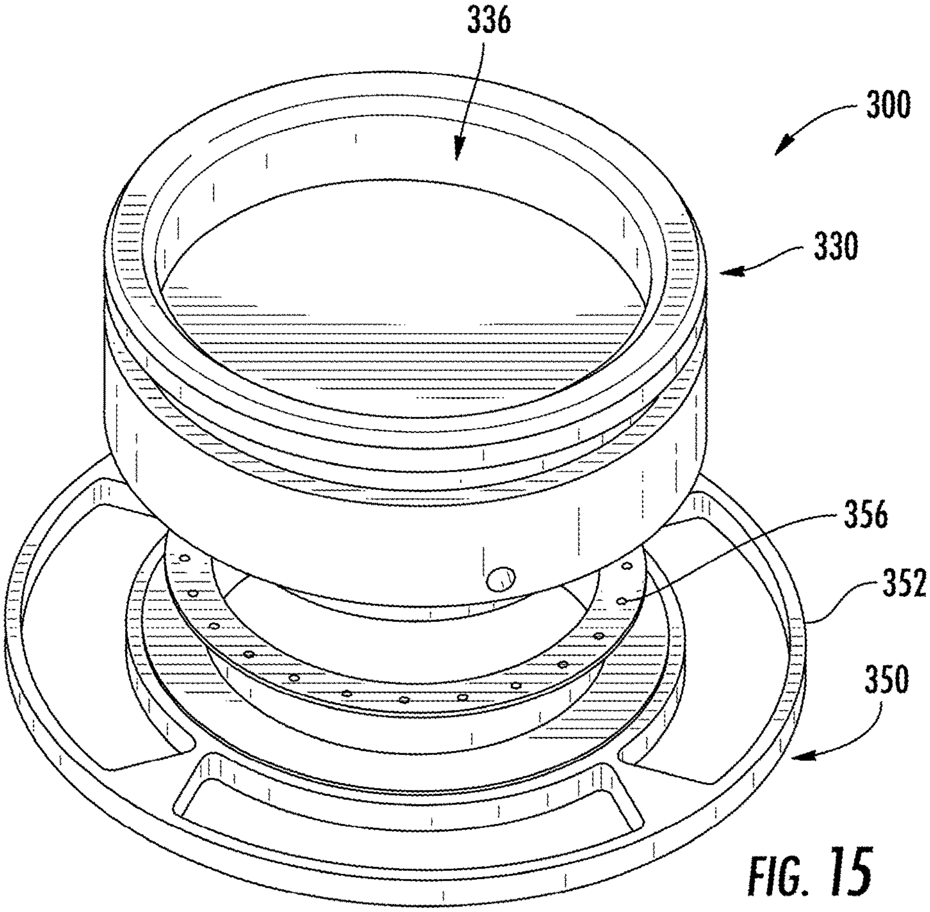
FIG. 15 is a top perspective view of the plug and the suture ring of FIG. 12 separated from one another.
Figure 16:
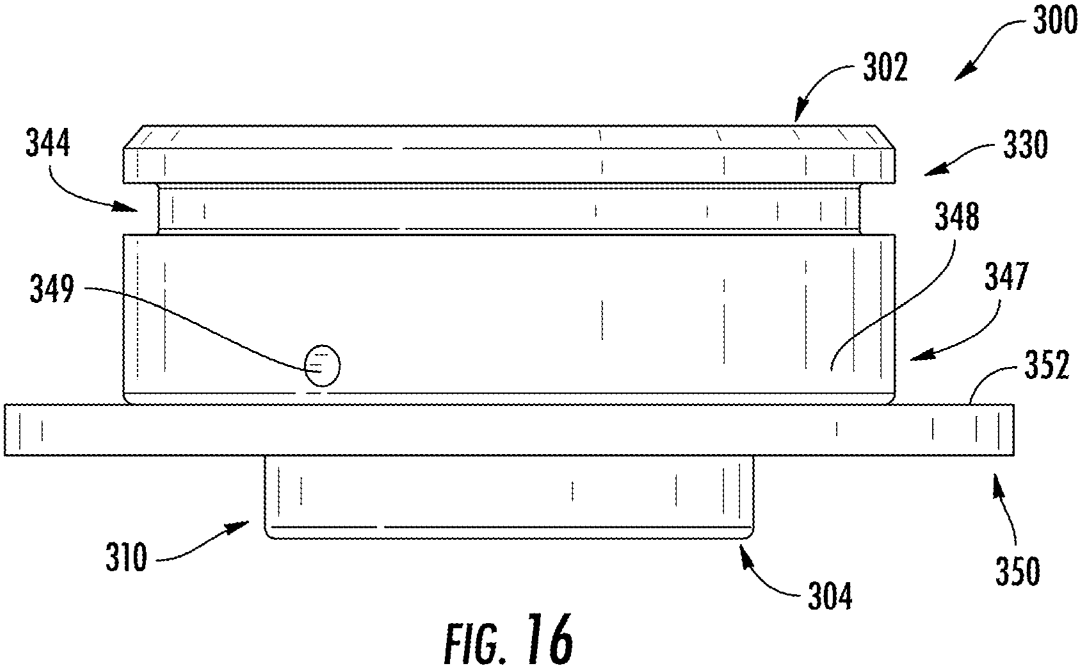
FIG. 16 is a side view of the plug and the suture ring of FIG. 12 coupled together.
Figure 17:
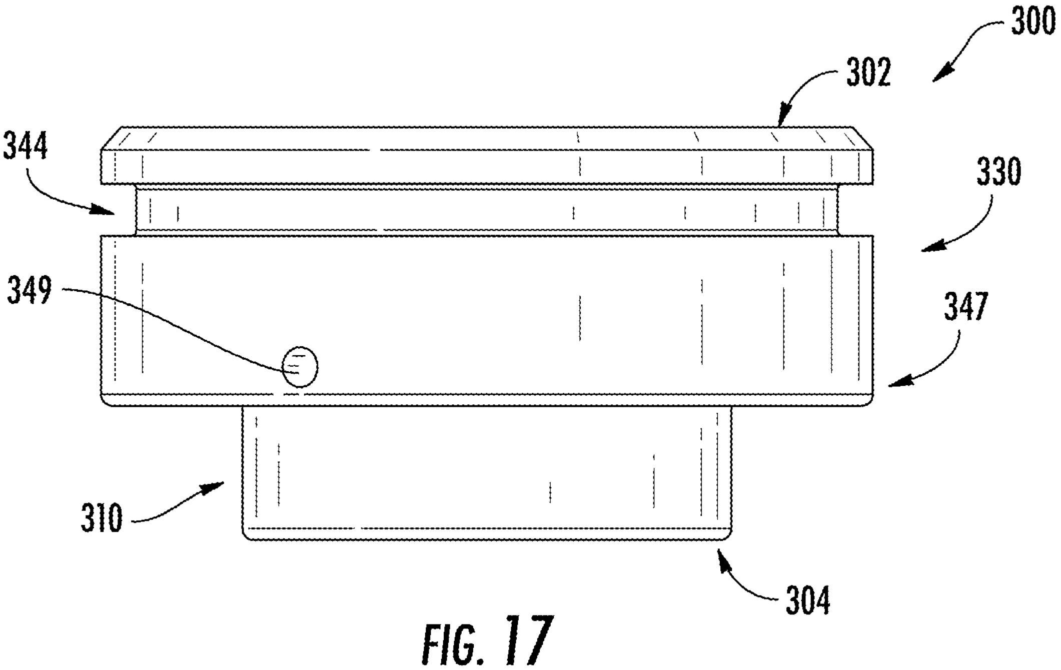
FIG. 17 is a side view of the plug of FIG. 12.
Figure 18:
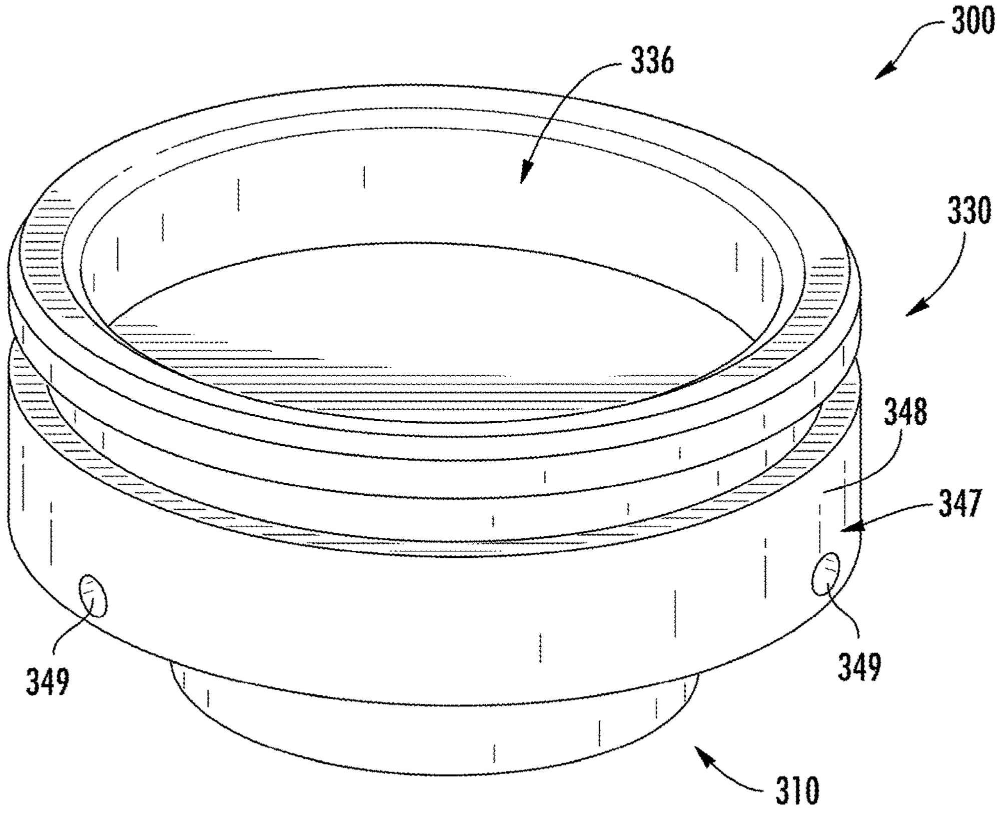
FIG. 18 is a top perspective view of the plug of FIG. 12.

The plug 200 may be coupled to the suture ring 150, as shown in FIG. 11, by inserting the distal portion 210 at least partially within the central opening of the suture ring 150 while the adjustable clamp 154 is in the unlocked configuration, and then adjusting the adjustable clamp 154 to the locked configuration by tightening the fastener 160. In this manner, the adjustable clamp 154 may be tightened to securely engage the third surface 218 of the distal portion 210 in the same manner as the adjustable clamp 154 engages an inlet tube of an LVAD. The third surface 218 of the distal portion receives pressure from the tightening of the adjustable clamp 154 of the suture ring 150 such that the pressure from the suture ring 150 couples the suture ring 150 to the distal portion 210 of the plug 200. When the plug 200 is used following removal of an LVAD from the suture ring 150 previously sutured to the cardiac tissue during the LVAD implantation, the tissue typically has healed around the suture ring 150, with tissue growth forming a strong bond between the suture ring 150 and the cardiac tissue of the heart 900. An advantageous aspect of the described approach for coupling the plug 200 to the suture ring 150 is that the technique does not require suturing or any involvement or disruption of the surrounding cardiac tissue of the heart 900. Furthermore, if the patient ever requires LVAD implantation again, the plug 200 can simply be removed from the suture ring 150 without any involvement or disruption of the surrounding cardiac tissue. Although the illustrated implementation provides one example of features for coupling the plug 200 to the suture ring 150, in other implementations, the suture ring 150 may include various other types any fastening features capable of coupling the plug 200 to the suture ring 150 without involving or disrupting the surrounding cardiac tissue.

Figure 21:
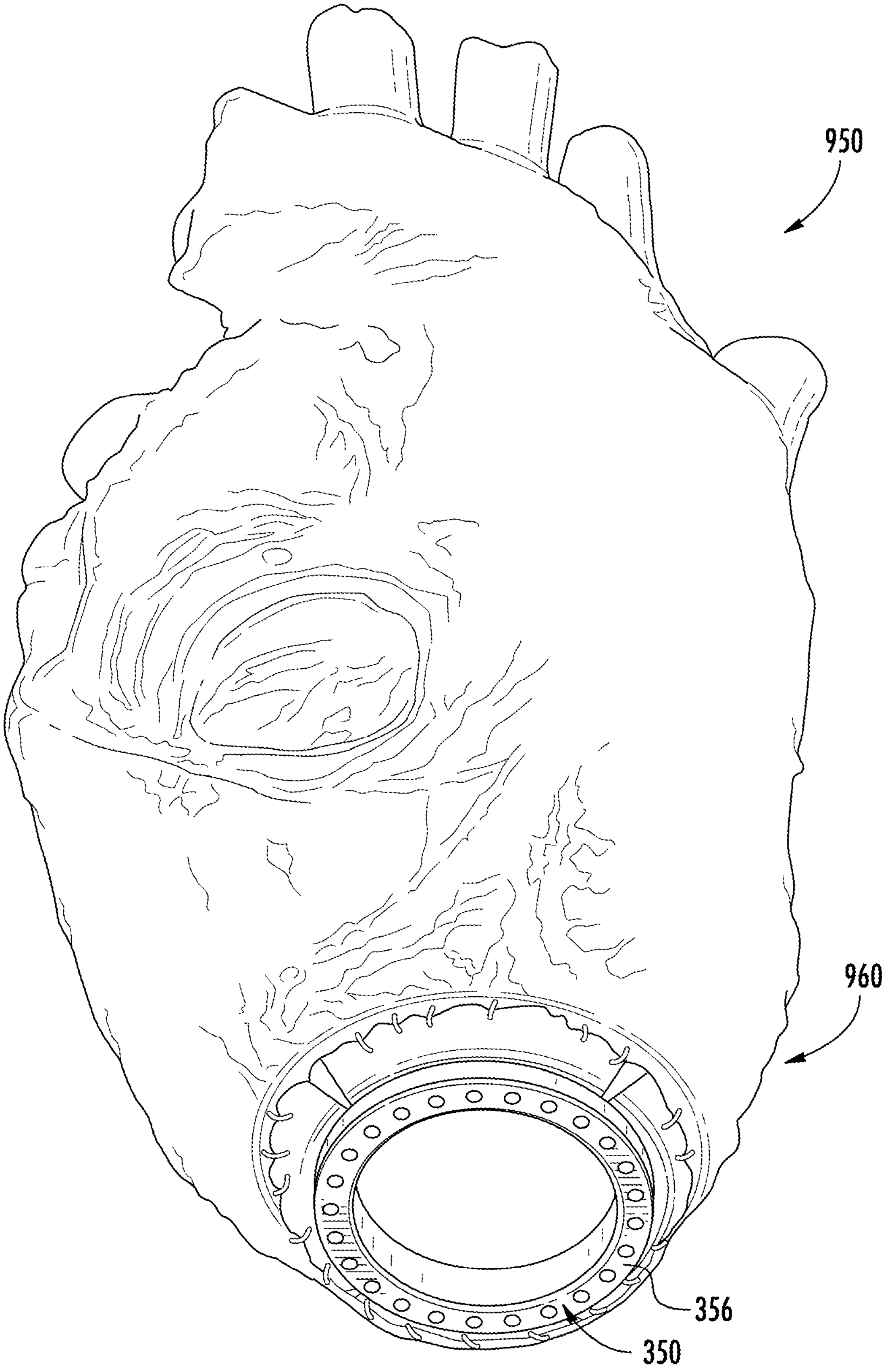
FIG. 21 is a perspective view of the suture ring of FIG. 12 coupled to a heart.
Figure 22:
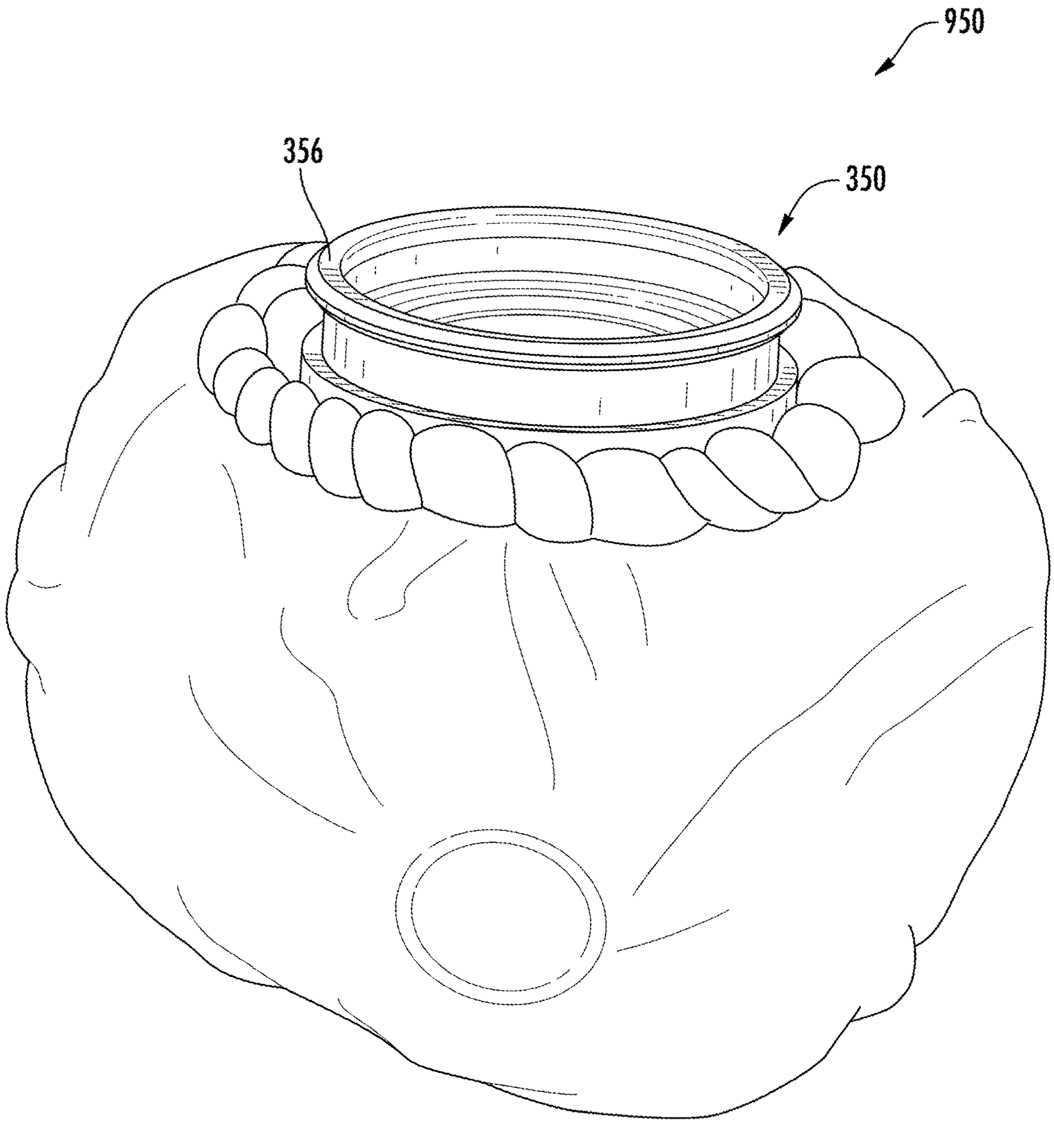
FIG. 22 is a perspective view of the suture ring of FIG. 12 coupled to a heart.

FIGS. 12-18 illustrate an example plug 300 (which also may be referred to as a "closure device," an "occlusion device," or simply a "device") in accordance with implementations of the disclosure. Certain similarities and differences between the plug 300 and the plugs 100, 200 will be appreciated from the drawings and the following description. The plug 300 may be configured for use with a suture ring 350, which may be attached to a patient's heart 950 by suturing, as shown in FIG. 21, for coupling an LVAD at the apex of the left ventricle 960. As described herein, the plug 300 may be configured for coupling to the suture ring 350, for example, upon removal of the LVAD therefrom, to prevent blood loss from the left ventricle 960 through the suture ring 350. Although the plug 300 is shown being used with suture ring 350, it will be appreciated that the plug 300 may be configured for use with other types of suture rings, in accordance with other implementations.

As shown, the plug 300 may have a proximal end 302 and a distal end 304 disposed opposite one another along a central axis of the plug 300. In some implementations, as shown, the plug 300 may be symmetric about the central axis of the plug 300. The plug 300 may include a distal portion 310 (which also may be referred to as an "anchoring portion" or a "first portion") and a proximal portion 330 (which also may be referred to as a "blocking portion" or a "second portion") coupled to one another. The distal portion 310 may extend from the distal end 304 toward the proximal end 302, and the proximal portion 330 may extend from the proximal end 302 toward the distal end 304. The distal portion 310 may be configured to engage with the suture ring 350 such that the distal portion 310 and the proximal portion 330 prevent blood loss from the left ventricle 960 while withstanding the beating heart pressure of the patient's heart 950. In some implementations, as shown, the distal portion 310 and the proximal portion 330 may be integrally formed with one another. In some implementations, the plug 300 may be formed of a metal, although other suitable materials may be used. In some implementations, the plug 300 may be formed of titanium, such as grade 5 titanium alloy (ASTM B348).

The distal portion 310 may include a distal cylindrical body 312 having a first diameter, a first surface 314 (which also may be referred to as a "distal surface"), a second surface 316 (which also may be referred to as a "proximal surface") spaced and disposed opposite the first surface 314 in the direction of the central axis of the plug 300, and a third surface 318 (which also may be referred to as an "outer circumferential surface") that extends from the first surface 314 to the second surface 316. As shown, the distal cylindrical body 312 may be centered on the central axis of the plug 300 and configured for being received at least partially within the central opening of the suture ring 350. In some implementations, the first surface 314 of the distal portion 310 may be smooth and highly polished. In some implementations, the first surface 314 of the distal portion 310 may extend beyond the distal end of the suture ring 350 when the plug 300 is coupled with the suture ring 350.

The proximal portion 330 may include a proximal cylindrical body having a first surface 332 (which also may be referred to as a "distal surface"), a second surface 334 (which also may be referred to as a "proximal surface") spaced and disposed opposite the first surface 332 in the direction of the central axis of the plug 300, and a third surface 342 (which also may be referred to as an "outer circumferential surface") that extends from the first surface 332 to the second surface 334. As shown, the proximal cylindrical body of the proximal portion 330 may have a second diameter that is greater than the first diameter of the distal cylindrical body 312 of the distal portion 310. In this manner, proximal cylindrical body of the proximal portion 330 may extend radially outward relative to the distal portion 310. As shown, the proximal cylindrical body may be centered on the central axis of the plug 300 and configured for extending over the proximal end of the suture ring 350 when the distal cylindrical body 312 is received at least partially within the central opening of the suture ring 350. In some implementations, as shown, the first surface 332 of the proximal cylindrical body of the proximal portion 330 may be adjacent and directly coupled to the second surface 316 of the distal cylindrical body 312 of the distal portion 310. In some implementations, the first surface 332 and the second surface 334 of the blocking portion 330 may be continuous. Also, similar to the distal end of the distal portion 310, the proximal end of the proximal portion 330 may be chamfered to avoid harsh sharp edges that could be harmful to the heart or internal organs of the patient.

The proximal portion 330 also may include an annular protrusion 347 that extends from the first surface 332 of the proximal portion 330. As shown, the annular protrusion 347 may extend toward the distal end of the plug 300 and encircle a portion of the distal cylindrical body 312. In this manner, the annular protrusion 347 and the portion of the distal cylindrical body 312 may define an annular space therebetween, with the annular space being configured for receiving a portion of the suture ring 350 therein such that the annular protrusion 347 encircles the portion of the suture ring 350. As shown, the annular protrusion 347 has an outer surface 348 that defines a plurality of thru holes 349 (which also may be referred to as "threaded fastener openings") that extend radially through the annular protrusion 347 from the outer surface 348 to the annular space. In some implementations, as shown, the annular protrusion 347 may define three thru holes 349 that are evenly spaced around the annular protrusion 347. Although, in other implementations, the plug 300 defines any suitable number of the thru holes 349 capable of coupling the plug 300 to the suture ring 350.

As shown, the plug 300 may include a cavity 336 extending from the proximal end 302 toward the distal end 304 of the plug 300. The cavity 336 may extend at least partially into the proximal portion 330. In some implementations, the cavity 336 may be defined entirely within the proximal portion 330. In other implementations, the cavity 336 may extend through the proximal portion 330 and into the distal portion 310 but may terminate at a location spaced apart from the distal end of the distal portion 310. In some implementations, as shown, the cavity 336 may be cylindrical. In some implementations, the cavity 336 may have different regions having different diameters, for example, with a larger diameter region defined in the proximal portion 330 and a smaller diameter region defined in the distal portion 310. The size, shape, and extend of the cavity 336 may be selected to minimize the weight of the plug 300 in order to not put excessive strain on the heart 950 when the plug 300 is coupled to the suture ring 350, while maintaining the structural integrity of the plug 300. In some implementations, as shown, the cavity 336 may be defined by a plurality of smooth, rounded edges that extend circumferentially around the cavity 336.

The plug 300 may include one or more features that are configured to be engaged by a tool to facilitate positioning of the plug 300 during implantation or removal of the plug 300. For example, the proximal portion 330 may include one or more recesses defined in the third surface 342 of the proximal cylindrical body and configured for being engaged by a tool to facilitate placement of the plug 300 relative to the suture ring 350 or removal of the plug 300 from the suture ring 350. In some implementations, as shown, the one or more recesses may include an annular proximal channel 344 that extends circumferentially along at least a portion of the third surface 342 of the proximal portion 330.

As shown, the suture ring 350 may include a first flange 352 (which also may be referred to as a "base flange" or a "base") defining the distal end of the suture ring 350, a body 354 (which also may be referred to as a "tubular body") extending proximally from the first flange 352, and a second flange 356 extending from the body 354 and defining the proximal end of the suture ring 350. In some implementations, the first flange 352, the body 354, and the second flange 356 may be integrally formed with one another. In some implementations, the first flange 352, the body 354, and the second flange 356 may be formed of a metal, such as titanium, although other suitable materials may be used. The first flange 352 may encircle the central opening of the suture ring 350 and be configured for engaging the outer surface of the patient's heart 950 when the suture ring 350 is attached thereto. In some implementations, as shown, the first flange 352 may include a plurality of openings extending therethrough to facilitate suturing of the suture ring 350 to the heart 950. In some implementations, the suture ring 350 may include a fabric material that covers at least a portion of the first flange 352 to facilitate suturing of the suture ring 350 to the heart 950, as shown in FIG. 21. In some implementations, at least a portion of the second flange 356 and/or the body 354 may be covered in an elastomeric coating to facilitate formation of a seal between the suture ring 350 and the plug 300 or an LVAD coupled to the suture ring 350. As shown, the suture ring 350 generally corresponds to the suture ring of the Abbott™ Heartmate3 LVAD.

The plug 300 may be coupled to the suture ring 350 by inserting the distal portion 310 at least partially within the central opening of the suture ring 350 until the second flange 356 abuts the first surface 332 of the proximal portion 330, and then advancing threaded fasteners 358 through the thru holes 349 of the annular protrusion 347. In this manner, threaded fasteners 358 may engage the body 354 of the suture ring 350, between the first flange 352 and the second flange 356, and be tightened to securely couple the suture ring 350 to the plug 300. When the plug 300 is used following removal of an LVAD from the suture ring 350 previously sutured to the cardiac tissue during the LVAD implantation, the tissue typically has healed around the suture ring 350, with tissue growth forming a strong bond between the suture ring 350 and the cardiac tissue of the heart 950. An advantageous aspect of the described approach for coupling the plug 300 to the suture ring 350 is that the technique does not require suturing or any involvement or disruption of the surrounding cardiac tissue of the heart 950. Furthermore, if the patient ever requires LVAD implantation again, the plug 300 can simply be removed from the suture ring 350 without any involvement or disruption of the surrounding cardiac tissue. Although the illustrated implementation provides one example of features for coupling the plug 300 to the suture ring 350, in other implementations, the suture ring 350 may include various other types any fastening features capable of coupling the plug 300 to the suture ring 350 without involving or disrupting the surrounding cardiac tissue.

Figure 19:
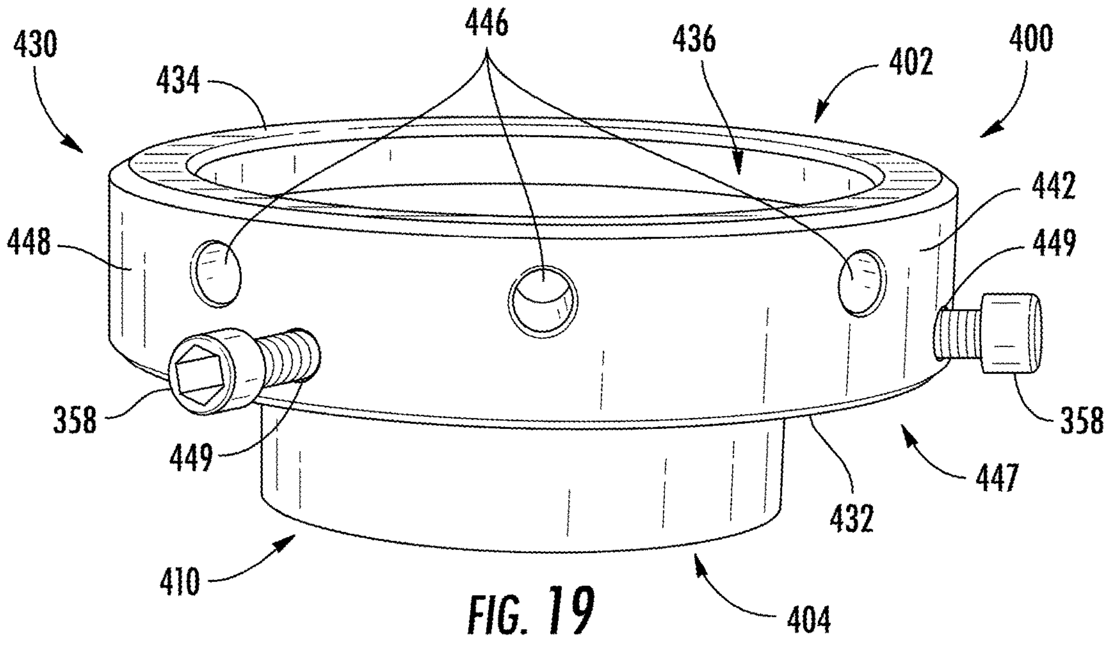
FIG. 19 is a top perspective view of an example plug in accordance with implementations of the present disclosure, as may be used with the suture ring of FIG. 12.
Figure 20:
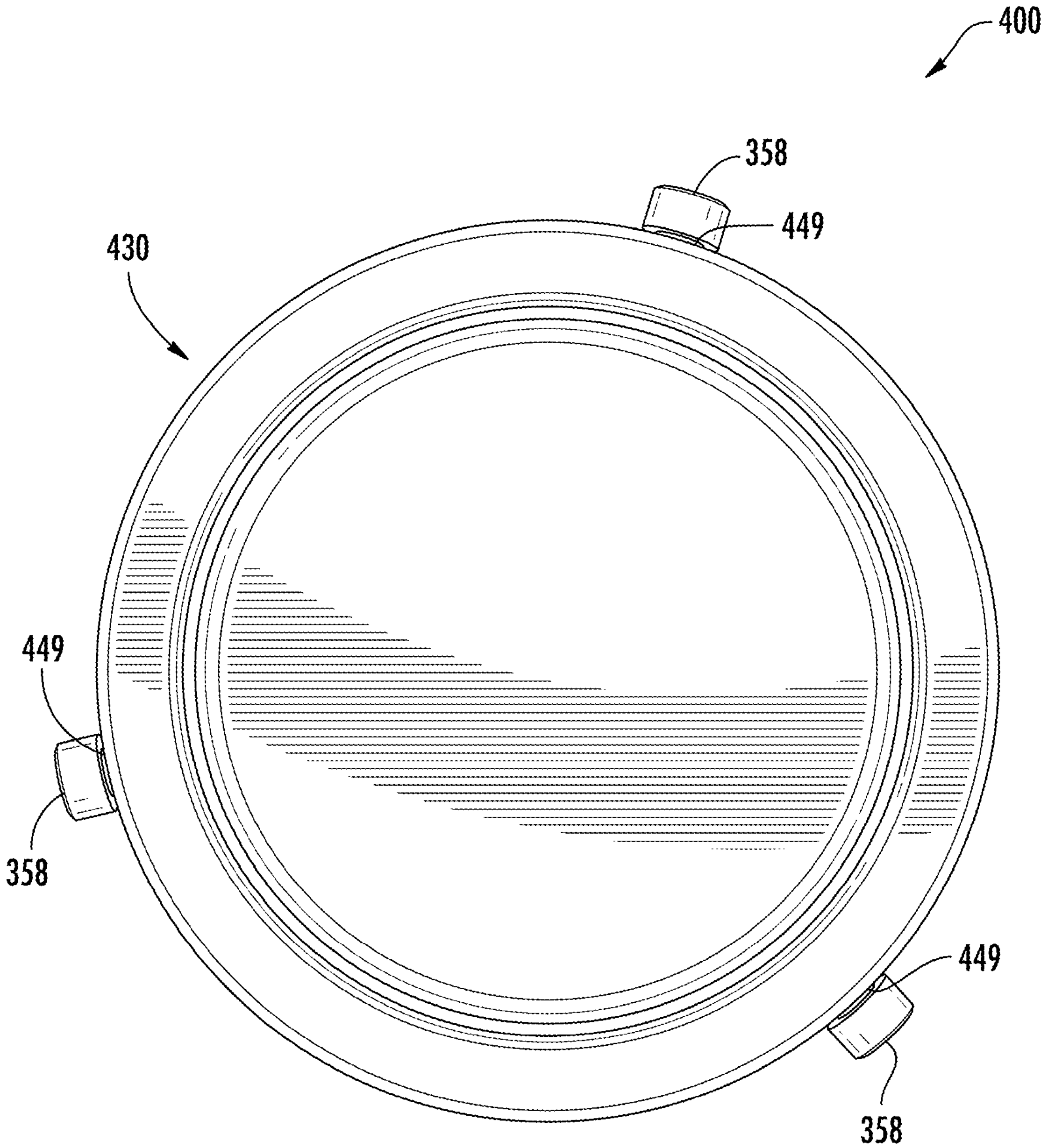
FIG. 20 is a top view of the plug of FIG. 19.

FIGS. 19 and 20 illustrate an example plug 400 (which also may be referred to as a "closure device," an "occlusion device," or simply a "device") in accordance with implementations of the disclosure. Certain similarities and differences between the plug 400 and the plugs 100, 200, 300 will be appreciated from the drawings and the following description. The plug 400 may be configured for use with the suture ring 350, which may be attached to a patient's heart 950 by suturing, as shown in FIG. 21, for coupling an LVAD at the apex of the left ventricle 960. As described herein, the plug 400 may be configured for coupling to the suture ring 350, for example, upon removal of the LVAD therefrom, to prevent blood loss from the left ventricle 960 through the suture ring 350. Although the plug 400 is shown being used with suture ring 350, it will be appreciated that the plug 400 may be configured for use with other types of suture rings, in accordance with other implementations.

As shown, the plug 400 may have a proximal end 402 and a distal end 404 disposed opposite one another along a central axis of the plug 400. In some implementations, as shown, the plug 400 may be symmetric about the central axis of the plug 400. The plug 400 may include a distal portion 410 (which also may be referred to as an "anchoring portion" or a "first portion") and a proximal portion 430 (which also may be referred to as a "blocking portion" or a "second portion") coupled to one another. The distal portion 410 may extend from the distal end 404 toward the proximal end 402, and the proximal portion 430 may extend from the proximal end 402 toward the distal end 404. The distal portion 410 may be configured to engage with the suture ring 450 such that the distal portion 410 and the proximal portion 430 prevent blood loss from the left ventricle 960 while withstanding the beating heart pressure of the patient's heart 950. In some implementations, as shown, the distal portion 410 and the proximal portion 430 may be integrally formed with one another. In some implementations, the plug 400 may be formed of a metal, although other suitable materials may be used. In some implementations, the plug 400 may be formed of titanium, such as grade 5 titanium alloy (ASTM B348).

The distal portion 410 may include a distal cylindrical body 412 having a first diameter, a first surface 414 (which also may be referred to as a "distal surface"), a second surface 416 (which also may be referred to as a "proximal surface") spaced and disposed opposite the first surface 414 in the direction of the central axis of the plug 400, and a third surface 418 (which also may be referred to as an "outer circumferential surface") that extends from the first surface 414 to the second surface 416. As shown, the distal cylindrical body 412 may be centered on the central axis of the plug 400 and configured for being received at least partially within the central opening of the suture ring 450. In some implementations, the first surface 414 of the distal portion 410 may be smooth and highly polished. In some implementations, the first surface 414 of the distal portion 410 may extend beyond the distal end of the suture ring 450 when the plug 400 is coupled with the suture ring 450.

The proximal portion 430 may include a proximal cylindrical body having a first surface 432 (which also may be referred to as a "distal surface"), a second surface 434 (which also may be referred to as a "proximal surface") spaced and disposed opposite the first surface 432 in the direction of the central axis of the plug 400, and a third surface 442 (which also may be referred to as an "outer circumferential surface") that extends from the first surface 432 to the second surface 434. As shown, the proximal cylindrical body of the proximal portion 430 may have a second diameter that is greater than the first diameter of the distal cylindrical body 412 of the distal portion 410. In this manner, proximal cylindrical body of the proximal portion 430 may extend radially outward relative to the distal portion 410. As shown, the proximal cylindrical body may be centered on the central axis of the plug 400 and configured for extending over the proximal end of the suture ring 450 when the distal cylindrical body 412 is received at least partially within the central opening of the suture ring 450. In some implementations, as shown, the first surface 432 of the proximal cylindrical body of the proximal portion 430 may be adjacent and directly coupled to the second surface 416 of the distal cylindrical body 412 of the distal portion 410. In some implementations, the first surface 432 and the second surface 434 of the blocking portion 430 may be continuous. Also, similar to the distal end of the distal portion 410, the proximal end of the proximal portion 430 may be chamfered to avoid harsh sharp edges that could be harmful to the heart or internal organs of the patient.

The proximal portion 430 also may include an annular protrusion 447 that extends from the first surface 432 of the proximal portion 430. As shown, the annular protrusion 447 may extend toward the distal end of the plug 400 and encircle a portion of the distal cylindrical body 412. In this manner, the annular protrusion 447 and the portion of the distal cylindrical body 412 may define an annular space therebetween, with the annular space being configured for receiving a portion of the suture ring 350 therein such that the annular protrusion 447 encircles the portion of the suture ring 350. As shown, the annular protrusion 447 has an outer surface 448 that defines a plurality of thru holes 449 (which also may be referred to as "threaded fastener openings") that extend radially through the annular protrusion 447 from the outer surface 448 to the annular space. In some implementations, as shown, the annular protrusion 447 may define three thru holes 449 that are evenly spaced around the annular protrusion 447. Although, in other implementations, the plug 400 defines any suitable number of the thru holes 449 capable of coupling the plug 400 to the suture ring 350.

As shown, the plug 400 may include a cavity 436 extending from the proximal end 402 toward the distal end 404 of the plug 400. The cavity 436 may extend at least partially into the proximal portion 430. In some implementations, the cavity 436 may be defined entirely within the proximal portion 430. In other implementations, the cavity 436 may extend through the proximal portion 430 and into the distal portion 410 but may terminate at a location spaced apart from the distal end of the distal portion 410. In some implementations, as shown, the cavity 436 may be cylindrical. In some implementations, the cavity 436 may have different regions having different diameters, for example, with a larger diameter region defined in the proximal portion 430 and a smaller diameter region defined in the distal portion 410. The size, shape, and extend of the cavity 436 may be selected to minimize the weight of the plug 400 in order to not put excessive strain on the heart 950 when the plug 400 is coupled to the suture ring 350, while maintaining the structural integrity of the plug 400. In some implementations, as shown, the cavity 436 may be defined by a plurality of smooth, rounded edges that extend circumferentially around the cavity 436.

The plug 400 may include one or more features that are configured to be engaged by a tool to facilitate positioning of the plug 400 during implantation or removal of the plug 400. For example, the proximal portion 430 may include one or more recesses defined in the third surface 442 of the proximal cylindrical body proximally with respect to the annular protrusion 447 and configured for being engaged by a tool to facilitate placement of the plug 400 relative to the suture ring 350 or removal of the plug 400 from the suture ring 350. In some implementations, as shown, the one or more recesses may include a plurality of holes 446 each extending radially with respect to the central axis of the plug 400. In some implementations, the plurality of holes 446 may include at least one, or several, pairs of the holes 446 diametrically opposed to one another. In some implementations, the plurality of holes 446 may include four or more of the holes 446 disposed in a circumferential array around the central axis of the plug 400. Although the illustrated implementation includes eight of the holes 446, a greater or lesser number of the holes 446 may be used. In some implementations, as shown, the holes 446 may be blind holes that terminate at locations spaced apart from the cavity 436. The holes 446 may be configured for receiving mating features of a tool, such as the tools 700, 800 described below. In some implementations, the holes 446 may not be diametrically opposed to one another, depending on the tool intended to be used with the plug 400.

Figure 23:
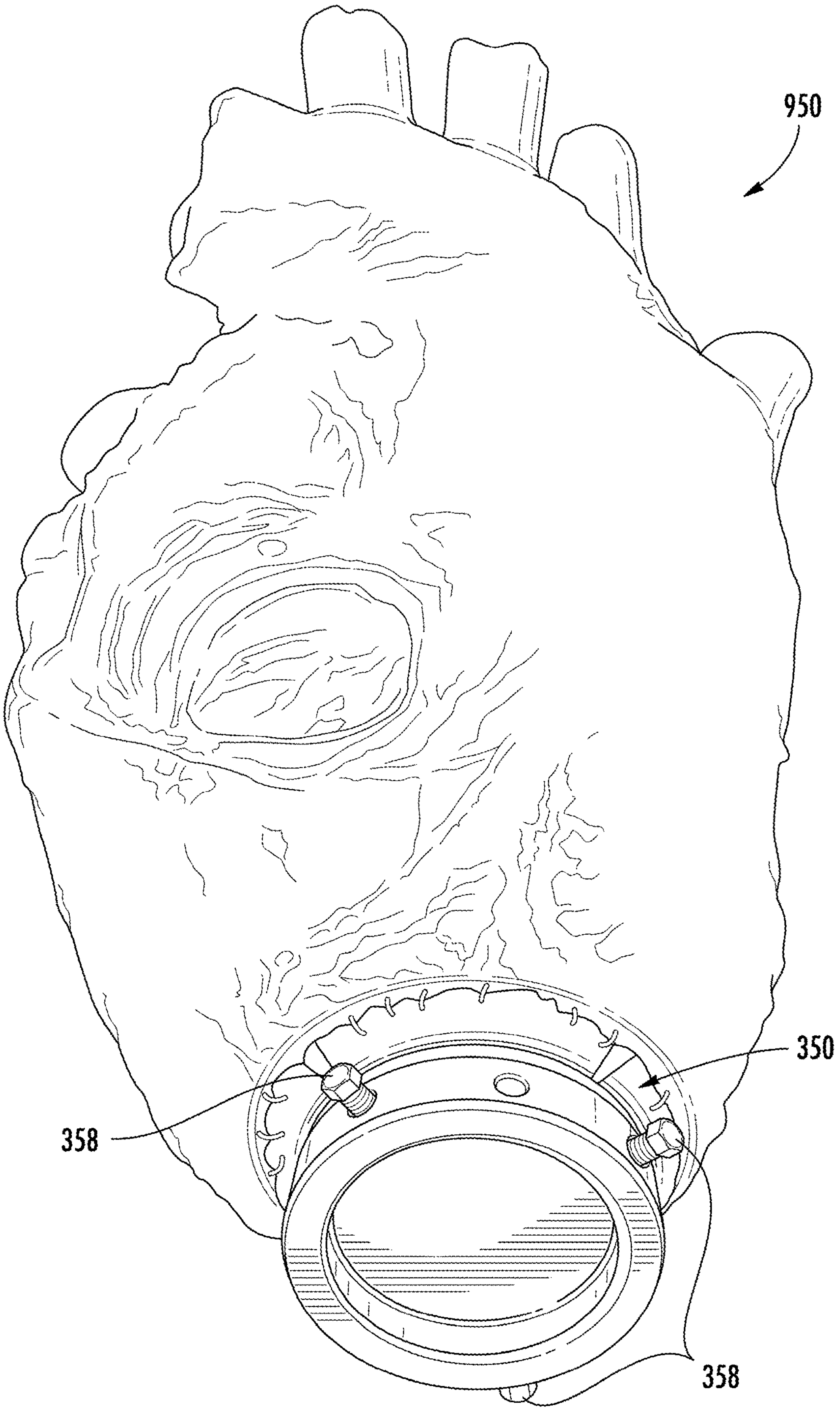
FIG. 23 is a perspective view of the plug of FIG. 19 and the suture ring of FIG. 12 coupled to a heart.

The plug 400 may be coupled to the suture ring 350, as shown in FIG. 23, by inserting the distal portion 410 at least partially within the central opening of the suture ring 350 until the second flange 356 abuts the first surface 432 of the proximal portion 430, and then advancing threaded fasteners 358 through the thru holes 449 of the annular protrusion 447. In this manner, the threaded fasteners 358 may engage the body 354 of the suture ring 350, between the first flange 352 and the second flange 356, and be tightened to securely couple the suture ring 350 to the plug 400. When the plug 400 is used following removal of an LVAD from the suture ring 350 previously sutured to the cardiac tissue during the LVAD implantation, the tissue typically has healed around the suture ring 350, with tissue growth forming a strong bond between the suture ring 350 and the cardiac tissue of the heart 950. An advantageous aspect of the described approach for coupling the plug 400 to the suture ring 350 is that the technique does not require suturing or any involvement or disruption of the surrounding cardiac tissue of the heart 950. Furthermore, if the patient ever requires LVAD implantation again, the plug 400 can simply be removed from the suture ring 350 without any involvement or disruption of the surrounding cardiac tissue. Although the illustrated implementation provides one example of features for coupling the plug 400 to the suture ring 350, in other implementations, the suture ring 350 may include various other types any fastening features capable of coupling the plug 400 to the suture ring 350 without involving or disrupting the surrounding cardiac tissue.

As discussed above with respect to the plugs 200, 400, the holes 246, 446 thereof may be configured to receive a tool. Specifically, a doctor may utilize the tool to linearly place or remove the plugs 200, 400 from the suture rings 150, 350. Linearly placing the plugs 200, 400 into the suture rings 150, 350 or linearly removing the plugs 200, 400 from the suture rings 150, 350 is advantageous for preventing complications during surgery and minimizing the amount of time required in surgery.

Figure 24:
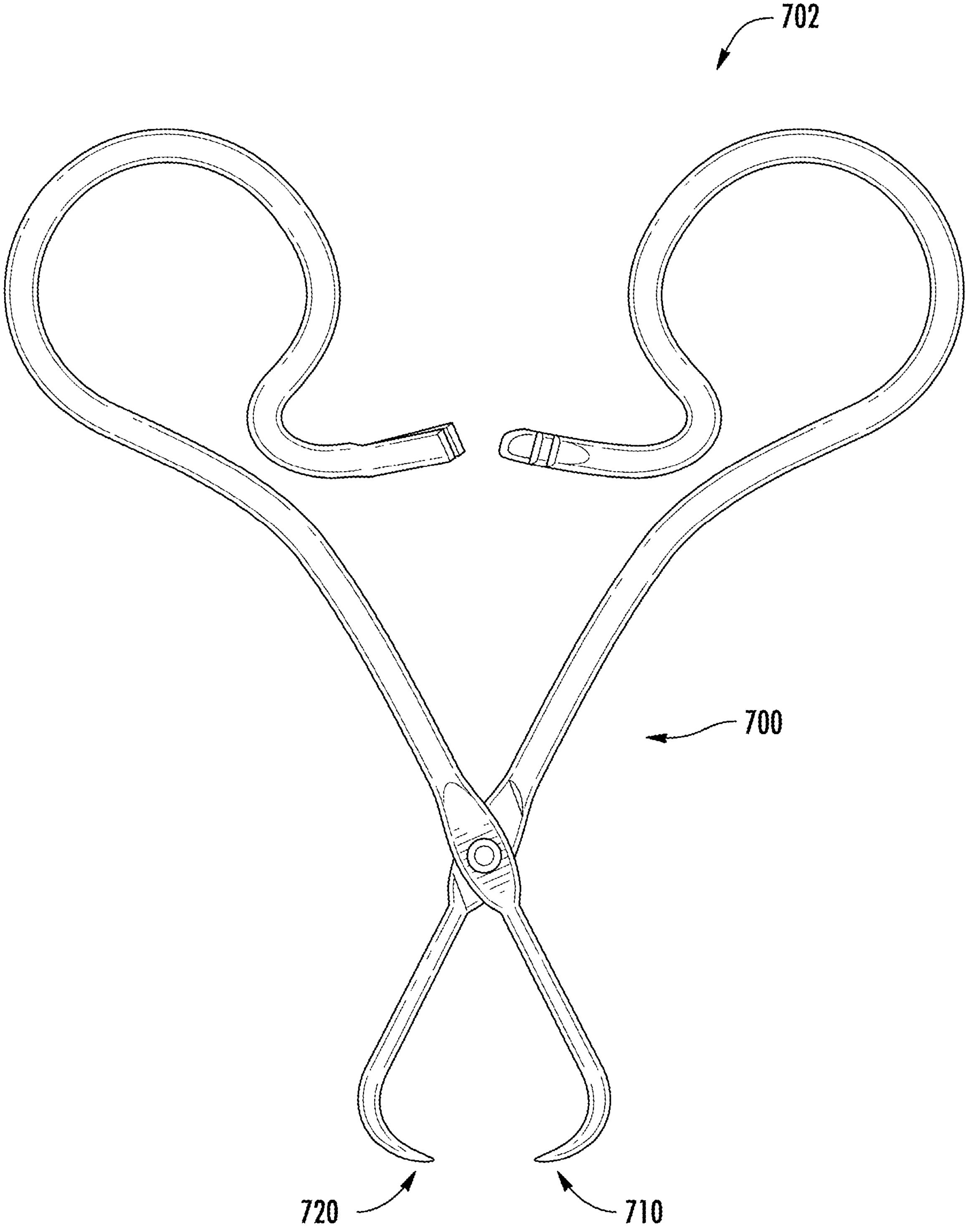
FIG. 24 is a front view of a tool for inserting and removing aforementioned implementations of plugs from corresponding suture rings.
Figure 25:
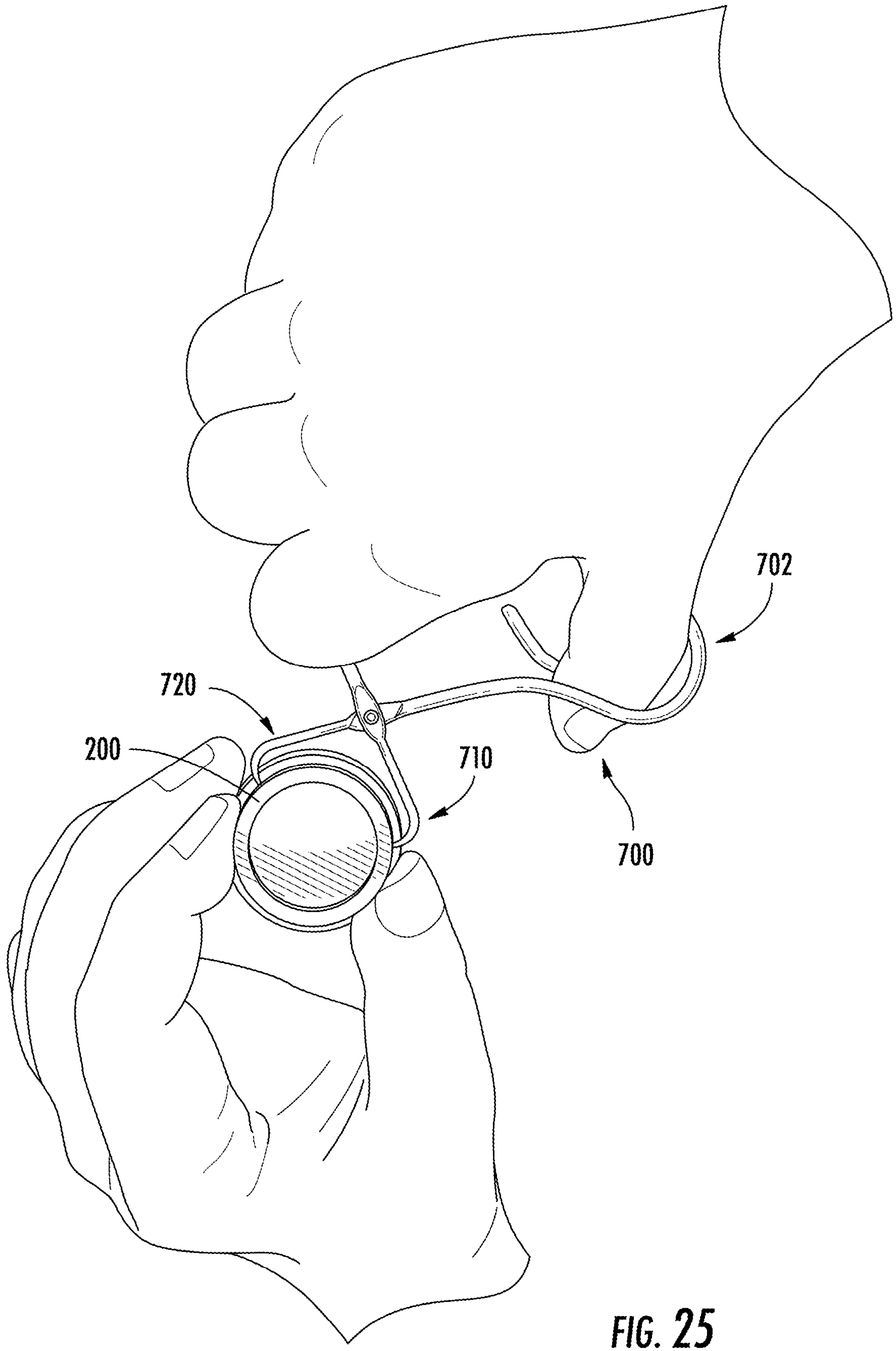
FIG. 25 is a top view showing how the tool of FIG. 24 interacts with a plug.

FIGS. 24 and 25 show one such implementation of a tool 700 that may be used to linearly place the plug 200, 400 into or remove the plug 200, 400 from the suture ring 150, 350. Although the tool 700 is shown with the plug 200 in FIG. 25, it will be appreciated that the tool 700 can be utilized with plug 400 or any implementation of the plug with at least two blind holes or divots to receive the tool 700. As shown, the tool 700 may include a user control portion 702, a first protrusion 710, and a second protrusion 720 opposite the first protrusion 710. The user (i.e., the doctor) may places their fingers within the user control portion 702 to adjust the space between the first protrusion 710 and the second protrusion 720 such that the space can receive and retain the plug 200, 400.

Figure 26:
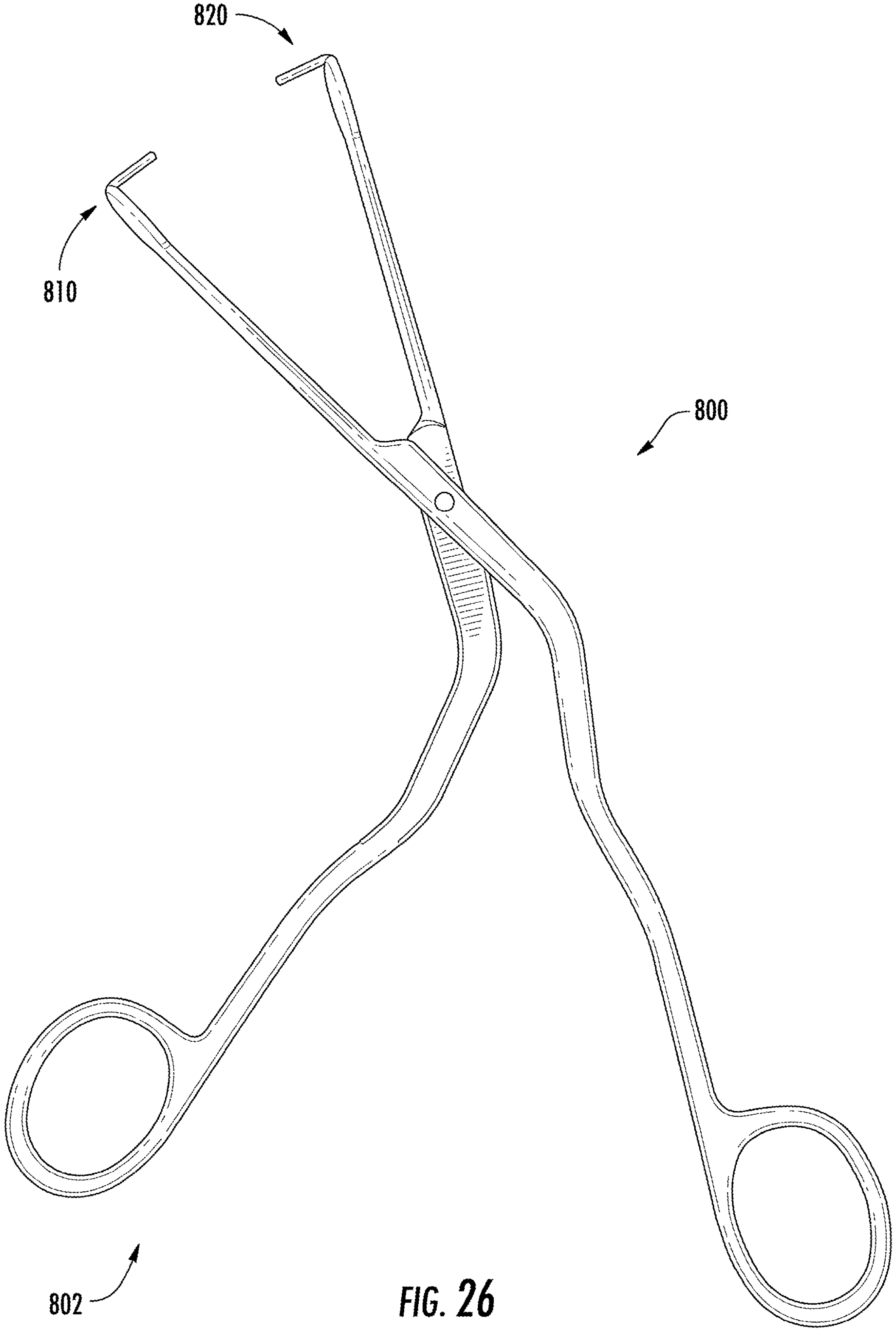
FIG. 26 is another implementation of a tool for inserting and removing aforementioned implementations of plugs from corresponding suture rings.

FIG. 26 shows another implementation of a tool 800 to linearly place the plug 200, 400 into or remove the plug 200, 400 from the suture ring 150, 350. The tool 800 also may include a user control portion 802, a first protrusion 810, and a second protrusion 820 opposite the first protrusion 810. However, as compared to the tool 700, the tool 800 has a longer length between the user control portion 802 and the first and second protrusions 810, 820. The longer length from the user control portion 802 and the first and second protrusions 810, 820 allows the user to be spaced further from the heart during surgery thus allowing the user to see the heart more easily.

Various other implementations include a system that includes a suture ring with an attachment mechanism that is configured to couple an LVAD to a patient's left ventricle and a plug. The suture ring is sewn into the apex of the left ventricle of a patient's heart. The plug is configured to couple to the suture ring via the attachment mechanism and block blood loss from the left ventricle while withstanding beating heart pressure.

Various other implementations include a method of explanting an LVAD from a suture ring. The method including detaching the LVAD from the suture ring, providing a plug, placing the plug within the suture ring, and coupling the plug to the suture ring.

In some implementations, the suture ring includes a coupling mechanism, and the coupling mechanism is configured to couple to the LVAD. In some implementations, coupling the plug to the suture ring further includes coupling the plug to the coupling mechanism.

A number of implementations have been described. Nevertheless, it will be understood that various modifications may be made without departing from the spirit and scope of the claims. Accordingly, other implementations are within the scope of the following claims.

Certain terminology is used herein for convenience only and is not to be taken as a limitation on the present claims. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. A plug for coupling to a suture ring attached to the apex of the left ventricle of a heart of a patient, the plug comprising:

a distal portion extending from a distal end of the plug toward a proximal end of the plug, the distal portion comprising a distal cylindrical body centered on a central axis of the plug and a distal end surface defining the distal end of the plug, the distal portion configured for being received at least partially within a central opening of the suture ring so the distal end surface is flush with a distal end of the suture ring, the distal cylindrical body having a first outer diameter; and a proximal portion coupled to the distal portion and extending from the proximal end of the plug toward the distal end of the plug, the proximal portion comprising a proximal cylindrical body centered on the central axis of the plug and configured for extending over a proximal end of the suture ring when the distal cylindrical body is received at least partially within the central opening of the suture ring, the proximal cylindrical body having a second outer diameter that is greater than the first outer diameter.

2. The plug of claim 1, further comprising a cavity extending from the proximal end of the plug toward the distal end of the plug.

3. The plug of claim 2, wherein the cavity is defined entirely within the proximal portion.

4. The plug of claim 2, wherein the cavity extends through the proximal portion and into the distal portion.

5. The plug of claim 2, wherein the cavity is cylindrical, wherein the cavity is centered on the central axis of the plug, and wherein the cavity is defined by a plurality of rounded edges.

6. The plug of claim 2, wherein the proximal portion further comprises one or more recesses defined in an outer circumferential surface of the proximal cylindrical body, wherein the one or more recesses are configured for being engaged by a tool to facilitate placement of the plug relative to the suture ring or removal of the plug from the suture ring.

7. The plug of claim 6, wherein the one or more recesses comprises an annular proximal channel extending circumferentially around the central axis of the plug.

8. The plug of claim 6, wherein the one or more recesses comprises a plurality of holes each extending radially with respect to the central axis of the plug.

9. The plug of claim 2, wherein the proximal portion further comprises an annular protrusion extending toward the distal end of the plug and encircling a portion of the distal cylindrical body.

10. The plug of claim 9, wherein the annular protrusion and the portion of the distal cylindrical body define an annular space therebetween, and wherein the annular space is configured for receiving a portion of the suture ring therein such that the annular protrusion encircles the portion of the suture ring.

11. The plug of claim 10, wherein the proximal portion further comprises a plurality of thru holes each extending radially with respect to the central axis of the plug from an outer circumferential surface of the annular protrusion to the annular space, wherein each of the thru holes is configured for receiving a fastener.

12. The plug of claim 1, wherein the distal portion further comprises an annular distal channel extending circumferentially around the central axis of the plug, wherein the annular distal channel is configured for positioning within the central opening of the suture ring.

13. The plug of claim 12, further comprising an O-ring disposed at least partially within the annular distal channel and configured for forming a seal between the distal portion and a portion of the suture ring defining the central opening of the suture ring.

14. The plug of claim 1, wherein the proximal portion further comprises one or more recesses defined in an outer circumferential surface of the proximal cylindrical body, wherein the one or more recesses are configured for being engaged by a tool to facilitate placement of the plug relative to the suture ring or removal of the plug from the suture ring.

15. The plug of claim 14, wherein the one or more recesses comprises an annular proximal channel extending circumferentially around the central axis of the plug, wherein the one or more recesses comprises a plurality of holes each extending radially with respect to the central axis of the plug.

16. The plug of claim 1, wherein the proximal portion further comprises an annular protrusion extending toward the distal end of the plug and encircling a portion of the distal cylindrical body.

17. The plug of claim 16, wherein the annular protrusion and the portion of the distal cylindrical body define an annular space therebetween, and wherein the annular space is configured for receiving a portion of the suture ring therein such that the annular protrusion encircles the portion of the suture ring.

18. The plug of claim 17, wherein the proximal portion further comprises a plurality of thru holes each extending radially with respect to the central axis of the plug from an outer circumferential surface of the annular protrusion to the annular space, wherein each of the thru holes is configured for receiving a fastener therethrough.

19. A system comprising:

a suture ring comprising:

an adjustable clamp disposed around a central opening of the suture ring and configured for adjusting between an unlocked configuration and a locked configuration, the adjustable clamp defining a distal end of the suture ring; and a fastener coupled to the adjustable clamp and configured for adjusting the adjustable clamp between the unlocked configuration and the locked configuration; and a plug comprising:

a distal portion extending from a distal end of the plug toward a proximal end of the plug, the distal portion comprising a distal cylindrical body centered on a central axis of the plug and a distal end surface defining the distal end of the plug, the distal portion configured for being received at least partially within the central opening of the suture ring so the distal end surface is flush with the distal end of the suture ring, the distal cylindrical body having a first outer diameter; and a proximal portion coupled to the distal portion and extending from the proximal end of the plug toward the distal end of the plug, the proximal portion comprising a proximal cylindrical body centered on the central axis of the plug and configured for extending over a proximal end of the suture ring when the distal cylindrical body is received at least partially within the central opening of the suture ring, the proximal cylindrical body having a second outer diameter that is greater than the first outer diameter;

wherein the adjustable clamp is configured for securing the plug to the suture ring when the distal cylindrical body is received at least partially within the central opening of the suture ring and the adjustable clamp is in the locked configuration.

20. A system comprising:

a suture ring comprising:

a proximal flange disposed around a central opening of the suture ring; and a tubular body coupled to the proximal flange and disposed around the central opening of the suture ring;

a plug comprising:

a distal portion extending from a distal end of the plug toward a proximal end of the plug, the distal portion comprising a distal cylindrical body centered on a central axis of the plug and configured for being received at least partially within the central opening of the suture ring, the distal cylindrical body having a first outer diameter; and a proximal portion coupled to the distal portion and extending from the proximal end of the plug toward the distal end of the plug, the proximal portion comprising:

a proximal cylindrical body centered on the central axis of the plug and configured for extending over the proximal flange of the suture ring when the distal cylindrical body is received at least partially within the central opening of the suture ring, the proximal cylindrical body having a second outer diameter that is greater than the first outer diameter; and an annular protrusion extending toward the distal end of the plug and encircling a portion of the distal cylindrical body such that the annular protrusion and the portion of the distal cylindrical body define an annular space therebetween, the annular space being configured for receiving the proximal flange and at least a portion of the tubular body of the suture ring therein when the distal cylindrical body is received at least partially within the central opening of the suture ring; and a plurality of fasteners configured for extending through a plurality of thru holes defined in the annular protrusion and engaging the tubular body of the suture ring to secure the plug to the suture ring when the distal cylindrical body is received at least partially within the central opening of the suture ring.

* * * * *